US007910661B2

(12) United States Patent
Kozlowski et al.

(10) Patent No.: US 7,910,661 B2
(45) Date of Patent: Mar. 22, 2011

(54) THIOL-SELECTIVE WATER-SOLUBLE POLYMER DERIVATIVES

(75) Inventors: Antoni Kozlowski, Huntsville, AL (US); Remy F. Gross, III, Petaluma, CA (US); Samuel P. McManus, Huntsville, AL (US)

(73) Assignee: Nektar Therapeutics, San Carlos, CA (US)

( * ) Notice: Subject to any disclaimer, the term of this patent is extended or adjusted under 35 U.S.C. 154(b) by 1628 days.

(21) Appl. No.: 10/753,047

(22) Filed: Jan. 6, 2004

(65) Prior Publication Data

US 2005/0014903 A1     Jan. 20, 2005

Related U.S. Application Data

(60) Provisional application No. 60/438,555, filed on Jan. 6, 2003, provisional application No. 60/455,084, filed on Mar. 14, 2003.

(51) Int. Cl.
C08F 22/38 (2006.01)
(52) U.S. Cl. ............... 525/326.9; 525/330.3; 525/333.9
(58) Field of Classification Search ............... 525/326.9, 525/330.3, 333.9
See application file for complete search history.

(56) References Cited

U.S. PATENT DOCUMENTS

| 5,446,090 | A | * | 8/1995 | Harris | ............................ 525/54.1 |
| 5,516,703 | A | | 5/1996 | Caldwell et al. | |
| 5,739,208 | A | | 4/1998 | Harris | |
| 5,741,715 | A | * | 4/1998 | Ghoshal et al. | ............... 436/537 |
| 5,932,462 | A | | 8/1999 | Harris et al. | |

FOREIGN PATENT DOCUMENTS

| WO | 95/13312 | 5/1995 |
| WO | 01/47562 A3 | 7/2001 |

OTHER PUBLICATIONS

Huang et al. Bioconjugate Chem. 1998, 9, 612-217.*
Zalipsky et al., Bioconjugate Chem. Sep./Oct. 1999, vol. 10, No. 5, 703-708.*
Enzon Pharmaceuticals, Macromolecular Engineering Technologies, pp. 1-14, (2004).
Nektar™—Transforming Therapeutics, Nektar Molecule Engineering: Polyethylene Glycol and Derivatives for Advanced PEGylation, pp. 1-20, (Catalog—2003).
Nektar™—Transforming Therapeutics, Nektar Molecule Engineering: Polyethylene Glycol and Derivatives for Advanced PEGylation, pp. 1-24, (Catalog—2004).
NOF Corporation, "PEG Derivatives Phospholipid and Drug Delivery Materials for Pharmaceuticals", pp. 1-46, (Catalogue 2003-1st).
NOF Corporation, "PEG Derivatives Phospholipid and Drug Delivery Materials for Pharmaceuticals", p. 1-46, (Catalogue 2003-2nd).
Polypure, Products; PEG amines; PEG acids and amino acids; PEG thiols and disulfides; Biotins, (Apr. 2004).
Polypure, Products; PEG amines; PEG acids and amino acids; PEG thiols and disulfides; Biotins, (Apr. 2005).
Quanta Biodesign, Labeling, Derivatization and Crosslinking Reagents for Biological and Related Materials with dPEG™, p. 1-38, (Mar. 12, 2004).
Quanta Biodesign, Labeling, Modification and Crosslinking Reagents incorporating our unique momodispersed dPEG™ Technology, p. 1-31, (Nov. 5, 2004).
Quanta Biosesign, Ltd., Leading innovator, producer and provider of monodisperse discrete PEG™ (dPEG™) derivatives, (Product Catalog), p. 1-51, (Updated: Jul. 18, 2005).
Quanta Biosesign, Ltd., Leading innovator, producer and provider of monodisperse discrete PEG™ (dPEG™) derivatives, (Product Catalog), p. 1-51, (Updated: Nov. 17, 2005).
Shearwater Polymers, Inc., p. 2-49, (Catalog—Mar. 1995).
Shearwater Polymers, Inc., Polyethylene Glycol and Derivatives, p. 1-53, (Catalog—Jul. 1997).
Shearwater Polymers, Inc., Polyethylene Glycol and Derivatives, p. 1-50, (Catalog—2000).
Shearwater Corporation, Polyethylene Glycol and Derivatives for Biomedical Applications, p. 1-17, (Catalog—2001).
U.S. Appl. No. 10/750,996, filed Dec. 31, 2003, Kozlowski et al.
U.S. Appl. No. 10/751,274, filed Dec. 31, 2003, Kozlowski et al.
Akiyama et al., "Selective Synthesis of Heterobifuntional Poly(ethylene glycol) Derivatives Containig Both Mercapto and Acetal Terminals," Bioconjugate Chem. (2000), vol. 11, pp. 947-950.
Bettinger et al., "Convenient Polymer-Supported Synthetic Route to Heterobifunctional Polyethylene Glycols," Bioconjugate Chem. (1998), vol. 9, pp. 842-846.
Harris et al., "Synthesis of Polyethylene Glycol Thiol," Polym. Preper. (Am. Chem. Soc., Div. Polym. Chem.), 32(1), 154-155 (1991).
Herman et al., "End-group modification of a-hydro-w-methoxypoly(oxyethylene, 3a) Facile methods for the introduction of thiol-selective reactive end-group," Macromol. Chem. Phys. (1994), vol. 195, pp. 203-209.
Huang et al., "A Polyethylene Glycol Copolymer for Carrying and Releasing Multiple Copies of Cysteine-Containing Peptides," Bioconjugate Chem. (1998), vol. 9, pp. 612-617.
Kaiser et al., "Basic Studies on Heterobifunctional Biotin-PEG Conjugates with a 3-(4-Pyridyldithio)propionyl Marker on the Second Terminus," Bioconjugate Chem. (1997), vol. 8, pp. 545-551.
Li et al., "Chemical Modification of Surface Active Poly(ethylene oxide)-Poly(propylene oxide) Triblock Copolymers," Bioconjugate Chem. 1(996), vol. 7, pp. 592-599.
Musu et al., "Reversible Modification of Thoil-Containing Polypeptides with Poly(ethylene glycol) Through Formation of Mixed Disulfide Bonds: The Case of Papaya Proteinase III," Applied Biochem. and Biotech. (1996), vol. 56, pp. 243-263. Otsuka et al., "Quantitative and Reversible Lectin-Induced Association of Gold Nanoparticles Modified with a-Lactosyl-w-mercapto-poly(ethylene glycol)," J. Am. Chem. Soc. (2001), vol. 123, pp. 8226-8230.
Woghiren et al., "Protected Thiol-Polyethylene Glycol: A New Activated Polymer for Reversible Protein Modification," Bioconjugate Chem. 1(993), vol. 4, pp. 314-318.
Zalipsky, "Functionalized Poly(ethylene glycol) for Preparation of Biologically Relevant Conjugates," Bioconjugate Chem. (1995), vol. 6, pp. 150-165.
Zalipsky et al., "New Detachable Poly(ethylene glycol) Conjugates: Cysteine-Cleavable Lipopolymers Regenerating Natural Phospholipid, Diacyl Phosphatidylethanolamine," American Chem. Society (1999), vol. 10 No. 5, pp. 703-707.

(Continued)

*Primary Examiner* — Robert D. Harlan
(74) *Attorney, Agent, or Firm* — Mark A. Wilson

(57) ABSTRACT

The present invention provides water-soluble, polymer derivatives having a thiol-selective terminus suitable for selective coupling to thiol groups, such as those contained in the cysteine residues of proteins.

41 Claims, No Drawings

OTHER PUBLICATIONS

"Polyethylene Glycol and Derivatives for Biomedical Applications.," Shearwater Corporation, Catalog 2001, pp. 1-17.

Written Opinion of the International Searching Authority, corresponding to International Application No. PCT/US2004/001190, dated Jul. 2, 2004.

European Patent Office Communication dated Jan. 16, 2007.

European Patent Office Communication dated Aug. 9, 2007.

European Patent Office Communication dated Apr. 8, 2008.

IP Australia Communication dated Sep. 24, 2007.

Patent Office of the People's Republic of China First Office Action dated Nov. 10, 2006.

Patent Office of the People's Republic of China Second Office Action dated May 9, 2008.

Japanese Patent Office Notice of Reasons of Rejection dated Jul. 21, 2009.

Government of India Patent Office First Examination Report dated Mar. 2008.

* cited by examiner

THIOL-SELECTIVE WATER-SOLUBLE POLYMER DERIVATIVES

CROSS REFERENCE TO RELATED APPLICATIONS

This application claims the benefit of priority to U.S. provisional application Ser. No. 60/438,555 filed Jan. 6, 2003 and to U.S. provisional application Ser. No. 60/455,084, filed Mar. 14, 2003, both of which are incorporated herein by reference in their entirety.

FIELD OF THE INVENTION

The present invention relates to a method for preparing thiol-selective derivatives of a water-soluble polymer such as polyethylene glycol. In particular, the invention relates to: (i) a method for preparing polymers having a thiol, protected-thiol, or other group suitable for coupling to the thiol group of a protein or other active agent at at least one terminus, (ii) the thiol-selective polymers themselves, (iii) conjugates thereof, and (iv) methods for utilizing such polymers.

BACKGROUND OF THE INVENTION

Due to recent advances in biotechnology, therapeutic proteins and other biomolecules, e.g. antibodies and antibody fragments, can now be prepared on a large scale, making such biomolecules more widely available. Unfortunately, the clinical usefulness of potential therapeutic biomolecules is often hampered by their rapid proteolytic degradation, instability upon manufacture, storage or administration, or by their immunogenicity. Due to the continued interest in administering proteins and other biomolecules for therapeutic use, various approaches to overcoming these deficiencies have been explored.

One such approach which has been widely explored is the modification of proteins and other potentially therapeutic biomolecules by covalent attachment of a water-soluble polymer such as polyethylene glycol or "PEG" (Abuchowski, A., et al, J. Biol. Chem. 252 (11), 3579 (1977); Davis, S., et al., Clin. Exp Immunol., 46, 649-652 (1981). The biological properties of PEG-modified proteins, also referred to as PEG-conjugates or pegylated proteins, have been shown, in many cases, to be considerably improved over those of their non-pegylated counterparts (Herman, et al., Macromol. Chem. Phys., 195, 203-209 (1994). Polyethylene glycol-modified proteins have been shown to possess longer circulatory times in the body due to increased resistance to proteolytic degradation, and also to possess increased thermostability (Abuchowski, A., et al., J. Biol. Chem., 252, 3582-3586 (1977). A similar increase in bioefficacy is observed with other biomolecules, e.g. antibodies and antibody fragments (Chapman, A., Adv. Drug Del. Rev. 54, 531-545 (2002)).

Typically, attachment of polyethylene glycol to a drug or other surface is accomplished using an activated PEG derivative, that is to say, a PEG having at least one activated terminus suitable for reaction with a nucleophilic center of a biomolecule (e.g., lysine, cysteine and similar residues of proteins). Most commonly employed are methods based upon the reaction of an activated PEG with protein amino groups, such as those present in the lysine side chains of proteins. Polyethylene glycol having activated end groups suitable for reaction with the amino groups of proteins include PEG-aldehydes (Harris, J. M., Herati, R. S., Polym Prepr. (Am. Chem. Soc., Div. Polym. Chem), 32(1), 154-155 (1991), mixed anhydrides, N-hydroxysuccinimide esters, carbonylimadazolides, and chlorocyanurates (Herman, S., et al., Macromol. Chem. Phys. 195, 203-209 (1994)). Although many proteins have been shown to retain activity during PEG modification, in some instances, polymer attachment through protein amino groups can be undesirable, such as when derivatization of specific lysine residues inactivates the protein (Suzuki, T., et al., Biochimica et Biophysica Acta 788, 248-255 (1984)). Therefore, it would be advantageous to have additional methods for the modification of a protein by PEG using another target amino acid for attachment, such as cysteine. Attachment to protein thiol groups on cysteine may offer an advantage in that cysteines are typically less abundant in proteins than lysines, thus reducing the likelihood of protein deactivation upon conjugation to these thiol-containing amino acids.

Polyethylene glycol derivatives having a thiol-selective reactive end group include maleimides, vinyl sulfones, iodoacetamides, thiols, and disulfides. These derivatives have all been used for coupling to the cysteine side chains of proteins (Zalipsky, S. Bioconjug. Chem. 6, 150-165 (1995); Greenwald, R. B. et al. Crit. Rev. Ther. Drug Carrier Syst. 17, 101-161 (2000); Herman, S., et al., Macromol. Chem. Phys. 195, 203-209 (1994)). However, many of these reagents have not been widely exploited due to the difficulty in their synthesis and purification. For instance, the method of Woghiren, et al. (Woghiren, C., et al., Bioconjugate Chem., 4, 314-318 (1993)) requires a series of synthetic transformation and purification steps to form a particular thiol-protected PEG reagent. First, methoxy-PEG is reacted with tosyl chloride followed by a purification of the reaction product to recover the corresponding tosyl-PEG. Tosyl-PEG is then converted to the corresponding PEG-thioacetate by reaction with a thioacetate salt, followed by another purification step. Alcoholysis with methanol is then carried out on the PEG-thioacetate, followed by column chromatography to yield the purified thiolate salt, which is then reduced with dithiothreitol to form the corresponding PEG-thiol. The resulting PEG thiol is then purified by column chromatography. A protected form of the thiol is then prepared by reaction of the PEG-thiol with 4,4'-dipyridyl disulfide, followed by purification by column chromatography. In sum, Woghiren's methodology for transforming PEG to its thiol-protected form requires five different reaction steps and an additional five separate purification steps, making this and other similar synthetic approaches undesirable and extremely time-consuming.

Another significant deficiency in many of the existing routes to monofunctional thiol specific PEG derivatives is the inability, despite multiple purification steps, to remove difunctionalized PEG which arises from the diol that is present in the monofunctional PEG raw material.

Thus, there exists a need for a method for preparing high purity, activated PEG-thiols and other thiol-selective PEG derivatives that is both straightforward and simple, i.e., requiring a minimum number of reaction and purification steps, whilst maintaining the integrity of the PEG segment (i.e., is carried out under mild reaction conditions), and which can further provide high purity thiol-selective PEG derivatives in high yields. Such a method has been developed by the Applicants, to be described in greater detail below.

SUMMARY OF THE INVENTION

In one aspect, the present invention provides a method for preparing a thiol-selective derivative of a water-soluble polymer (i.e., a polymer having at least one terminus that is a thiol-selective group, that is to say, a group that reacts preferentially with thiols such as a thiol, a thiolate, or a protected thiol). More particularly, the method includes the steps of (i) providing a water-soluble polymer, comprising a water soluble polymer segment designated herein as "POLY", having a terminus activated with an electrophile (-E), designated generally herein as "POLY-E", followed by (ii) reacting such polymer with a reactant molecule comprising both a nucleophile (-NU) and a thiol-selective moiety under conditions effective to promote reaction between the electrophile and the nucleophile to form a water-soluble polymer having a thiol-selective terminus, designated herein as "POLY-S", where "S" in this usage indicates a thiol-selective moiety. Thiol-selective moieties that may be contained within the reactant molecule include thiol, protected thiol, disulfide, maleimide, vinyl sulfone, iodoacetamide, and orthopyridyl disulfide.

In one particular embodiment of the invention, the thiol-selective moiety is selected from the group consisting of thiol, protected thiol, and disulfide.

In instances in which the thiol-selective moiety contained in the reactant molecule is a disulfide bond, the method may further comprise the step of reducing the disulfide bond in POLY-S to form a water-soluble polymer having a terminal thiol group (designated herein as "POLY-SH").

In one embodiment of the invention, e.g., when the polymer provided in step (i) is an end-capped linear polymer or a mono-functionally-activated polymer having only one reactive electrophilic terminus, the POLY-S product composition from step (ii) comprises greater than about 95% mole percent of the desired mono-functionally substituted POLY-S. Preferably, in this embodiment, the polymer provided in step (i) is a polyalkylene oxide containing less than about 5% of a combination of polyalkylene oxide diol and/or a bifunctional electrophilically-activated derivative of a polyalkylene oxide diol, based upon overall polymer components.

In yet another related embodiment, e.g., when the starting polymer is an end-capped or monofunctionally-activated polymer having only one reactive electrophilic terminus, the POLY-S product from step (ii) comprises less than about 5% di-functionally-substituted POLY-S.

In a further embodiment, the polymer in step (i) comprises an electrophile (-E) that is a carboxylic acid or an activated carboxylic acid derivative. Such electrophiles include carboxylic acid, amide, carboxylic acid ester, carbonate ester, carbonic acid, acid halide, and anhydride. In one specific embodiment of the invention, the polymer in step (i) is an N-hydroxysuccinimidyl propionate or an N-hydroxysuccinimidyl butanoate derivative of polyethylene glycol.

In yet another embodiment, the electrophile, E, is a carboxylic acid or an activated carboxylic acid derivative, and POLY-E, or a precursor thereof, is purified prior to the reacting step. Preferred methods of purification include chemical and chromatographic methods. In a preferred embodiment of the method, POLY-E is purified by column chromatography prior to the reacting step. In yet a more specific embodiment, POLY-E is purified by ion exchange chromatography or IEC.

The reactant molecule includes a nucleophile (-NU). Suitable nucleophiles include primary amino, secondary amino, hydroxy, imino, thiol, thioester, and their anionic counterparts where applicable. In a particular embodiment, the reactant molecule comprises a nucleophile that is a primary or secondary amino group.

In yet another embodiment, the reactant molecule is a symmetrical disulfide reagent comprising identical nucleophiles (-NU), generally as end groups, wherein the reacting step results in the formation of a symmetrical polymer having a central disulfide bond. In a specific embodiment, the molecule for reaction with the electrophilically activated polymer is cystamine or cysteamine. Alternatively, the reactant molecule is N-(2-amino-ethyl)3-maleimido-propionamide, optionally protected as an amine salt.

In a further embodiment of the method wherein the thiol-selective moiety is a thiol, the method may further comprise the step of reacting the POLY-S thiol with a thiol or protected thiol group of a protein to form a disulfide-linked polymer-protein conjugate, designated generally herein as POLY-S-S-protein.

The invention further provides a disulfide-linked polymer protein conjugate produced by such method.

In another aspect, the invention encompasses a water-soluble polymer having a thiol-selective terminus produced by the above method, designated generally herein as POLY-S. Illustrative thiol-selective groups include thiol, protected thiol, disulfide, maleimide, vinyl sulfone, α-haloacetyl compounds such as iodoacetamide and iodoacetate, mercurials, aryl halides, diazoacetates, and orthopyridyl disulfide.

Water-soluble polymer segments suitable for use in the invention include polyvinylpyrrolidone, polyvinylalcohol, polyacryloylmorpholine, polyoxazoline, and polyoxyethylated polyols.

In a preferred embodiment of the invention, the polymer is a polyalkylene oxide such as polyethylene glycol (PEG).

A polymer of the invention may further comprise an end-capping group such as $C_1$-$C_{20}$ alkoxy, preferably methoxy, ethoxy or benzyloxy.

In yet another embodiment of the invention, the polymer, e.g., a polyethylene glycol polymer, has a nominal average molecular mass selected from the group consisting of from about 200 to about 100,000 daltons, or from about 200 to about 60,000 daltons, or from about 500 to about 40,000 daltons. In a preferred embodiment, the polymer has a molecular weight ranging from about 20,000 to about 40,000 daltons. One preferred polyethylene glycol polymer has a molecular weight of about 20,000 daltons.

Polymers suitable for use in methods and compositions of the invention may possess a number of different geometries including linear, branched, forked and multi-armed. Polymers having a linear structure include mono-functional, homodifunctional and heterobifunctional polymers.

In yet another embodiment, a polymer segment for use in the invention may comprise a hydolyzable linkage.

In another aspect, the invention provides a method for preparing a thiol derivative of a water-soluble polymer that includes the following steps. Step (i) comprises providing an electrophilically-activated polymer, designated herein specifically as POLY-$L_{0,1}$-E (I). In the preceding structure, POLY is a water-soluble polymer segment, L is an optional linker, where $L_0$ indicates the absence of a linker and $L_1$ indicates that such a linker is present, and E is an electrophile. Step (ii) comprises reacting POLY-$L_{0,1}$-E with a symmetrical disulfide reagent, designated more specifically herein as (NU-Y—S—)$_2$, wherein NU is a nucleophile, Y is a group interposed between "NU" and the thiol-selective group, in this case a disulfide, and S is a sulfur atom, under conditions effective to promote reaction between E and NU to thereby form POLY-$L_{0,1}$-X—Y—S—S—Y—X-$L_{0,1}$-POLY ((POLY-$L_{0,1}$-X—Y—S—)$_2$), (II), wherein X is a group resulting from the reaction between E and NU. Preferred Y groups are selected from the group consisting of alkylene, substituted alkylene, cycloalkylene, substituted cycloalkylene, aryl, and substituted aryl, comprising from about 2 to about 10 carbon atoms, In another embodiment, the method may further include the step of (iii) reducing the disulfide bond in (POLY-$L_{0,1}$-X—Y—S—)$_2$ to form POLY-$L_{0,1}$-X—Y—SH, (III), where "—SH" is a thiol.

Particular L's contained in the polymer include $C_1$-$C_{10}$ alkyl and $C_1$-$C_{10}$ substituted alkyl. In one embodiment, the linker is selected from the group consisting of $(CH_2)_{1,2,3,4 \text{ and } 5}$.

Representative E's include carboxylic acids or activated carboxylic acid derivatives such as carboxylic acid, carboxylic acid ester, amide, carbonate ester, carbonic acid, acid halide, and anhydride. In one particular embodiment, E is a succinimidyl ester.

NU's in the symmetrical disulfide reagent include amino, hydroxy, imino, and thiol. In one specific embodiment, NU is —$NH_2$.

Resulting X groups contained in POLY-$L_{0,1}$-X—Y—S—S—Y—X-$L_{0,1}$-POLY ((POLY-$L_{0,1}$-X—Y—S—)$_2$) include amide, carbamate, carbonate ester, ether, and thioester.

In one embodiment, POLY comprises the structure —$(CH_2CH_2O)_n CH_2CH_2$— wherein n ranges from 10 to about 4,000, preferably from about 20 to about 1,000.

In yet another embodiment, POLY is an end-capped polyalkylene oxide such as polyethylene glycol, L is $L_0$ or —$CH_2$—, and E is N-hydroxysuccinimidyl ester.

In yet another embodiment, the symmetrical disulfide reagent is cystamine, where NU is primary amino and Y is —$(CH_2)_2$—.

In yet another aspect, the invention provides a method for preparing a polymer-protein conjugate, said method comprising the steps of: (i) providing an electrophilically-activated polymer, POLY-$L_{0,1}$-E, wherein POLY, L, and E are as previously defined, (ii) reacting POLY-$L_{0,1}$-E with a symmetrical disulfide reagent, (NU-Y—S—)$_2$, wherein NU, Y, and S are as previously defined, under conditions effective to promote reaction between E and NU to form POLY-$L_{0,1}$-X—Y—S—S—Y—X-$L_{0,1}$-POLY ((POLY-$L_{0,1}$-X—Y—S—)$_2$), wherein X is a group resulting from the reaction between E and NU, (iii) reducing the disulfide bond in (POLY-$L_{0,1}$-X—Y—S—)$_2$ to form POLY-$L_{0,1}$-X—Y—SH, and (iv) reacting POLY-$L_{0,1}$-X—Y—SH with a thiol or protected thiol group of a protein to form a protein conjugate, POLY-$_{0,1}$-X—Y—S—S-protein, (V).

In one embodiment of the above method, the protein is a therapeutic protein.

In yet another aspect, the invention provides an activated polymer comprising the structure:

POLY-$L_{0,1}$-C(O)G-Y—S—W,   (VI)

In structure VI, G is a heteroatom selected from the group consisting of O, —NH, —$NR^2$ where $R^2$ is lower alkyl, and S, and W is H or a protecting group. The remaining variables are as previously defined. In structure VI, —C(O)G- is a particular embodiment of "X".

Linkers, $L_1$, for use in the activated polymer include aliphatic linkers of from one to ten carbon atoms. Particular linkers include $(CH_2)_{1,2,3,4 \text{ and } 5}$.

In one particular embodiment of this aspect of the invention, POLY is an end-capped polyethylene glycol, L is absent or is —$CH_2$—, G is —NH, and Y is $(CH_2)_2$.

Also provided herein are compositions comprising the above described polymers and their conjugates.

In yet another aspect, the invention provides a polymer-conjugate comprising the structure:

POLY-$L_{0,1}$-C(O)G-Y—S—S-A   (VII)

where "A" indicates an active agent, and "S-A" indicates the residue of an active agent having a thiol group.

In one embodiment of this aspect of the invention, the active agent is selected from the group consisting of proteins, peptides, and small molecules.

Also provided herein is a method for delivering a bioactive agent to a subject in need thereof by administering a polymer-conjugate of the invention.

These and other objects and features of the invention will become more fully apparent when read in conjunction with the following detailed description.

DETAILED DESCRIPTION OF THE INVENTION

Definitions

The following terms as used herein have the meanings indicated. As used in the specification, and in the appended claims, the singular forms "a", "an", "the", include plural referents unless the context clearly dictates otherwise.

"Thiol selective derivative", in the context of a polymer of the invention, means a polymer having at least one terminus that is a thiol-reactive group. Preferentially, a thiol-selective group is one that reacts preferentially with thiol groups. A thiol-selective polymer of the invention will preferably be fairly selective for thiol groups under certain reaction conditions. Exemplary thiol-selective groups include maleimide, vinyl sulfone, orthopyridyl disulfide, iodoacetamide, thiol (—SH), thiolate (—S—), or protected thiol, that is to say, a thiol group in its protected form. Typical thiol protecting groups include thioether, thioester, or disulfide. Exemplary protecting groups for thiols can be found in Greene, T., and Wuts, Peter G. M., "PROTECTIVE GROUPS IN ORGANIC SYNTHESIS, Chapter 6, 3$^{rd}$ Edition, John Wiley and Sons, Inc., New York, 1999 (p. 454-493).

"Activated carboxylic acid" or "activated carboxylic acid derivative" means a functional derivative of a carboxylic acid that is more reactive than the parent carboxylic acid, in particular, with respect to nucleophilic acyl substitution. Activated carboxylic acids include but are not limited to acid halides (such as acid chlorides), anhydrides, amides and esters.

"PEG" or "poly(ethylene glycol)" as used herein, is meant to encompass any water-soluble poly(ethylene oxide). Typically, PEGs for use in the present invention will comprise one of the two following structures: "—$(CH_2CH_2O)_n$—" or "—$(CH_2CH_2O)_{n-1}CH_2CH_2$—," depending upon whether or not the terminal oxygen(s) has been displaced, e.g., during a synthetic transformation. The variable (n) ranges from 3 to 4000, and the terminal groups and architecture of the overall PEG may vary. When PEG further comprises a linker moiety (to be described in greater detail below), the atoms comprising the linker, when covalently attached to a PEG segment, do not result in formation of (i) an oxygen-oxygen bond (—O—O—, a peroxide linkage), or (ii) a nitrogen-oxygen bond (N—O, O—N). "PEG" means a polymer that contains a majority, that is to say, greater than 50%, of subunits that are —$CH_2CH_2O$—. PEGs for use in the invention include PEGs having a variety of molecular weights, structures or geometries (e.g., branched, linear, forked PEGs, dendritic, and the like), to be described in greater detail below.

"PEG diol", also known as alpha-,omega-dihydroxylpoly (ethylene glycol), can be represented in brief form as HO-PEG-OH, where PEG is as defined above.

"Water-soluble", in the context of a polymer of the invention or a "water-soluble polymer segment" is any segment or polymer that is soluble in water at room temperature. Typically, a water-soluble polymer or segment will transmit at least about 75%, more preferably at least about 95% of light, transmitted by the same solution after filtering. On a weight basis, a water-soluble polymer or segment thereof will preferably be at least about 35% (by weight) soluble in water, more preferably at least about 50% (by weight) soluble in water, still more preferably about 70% (by weight) soluble in water, and still more preferably about 85% (by weight) soluble in water. It is most preferred, however, that the water-soluble polymer or segment is about 95% (by weight) soluble in water or completely soluble in water.

An "end-capping" or "end-capped" group is an inert or non-reactive group present on a terminus of a polymer such as PEG. An end-capping group is one that does not readily undergo chemical transformation under typical synthetic reaction conditions. An end capping group is generally an alkoxy group, —OR, where R is an organic radical comprised of 1-20 carbons and is preferably lower alkyl (e.g., methyl, ethyl) or benzyl. "R" may be saturated or unsaturated, and includes aryl, heteroaryl, cyclo, heterocyclo, and substituted forms of any of the foregoing. For instance, an end capped PEG will typically comprise the structure "RO—(CH$_2$CH$_2$O)$_n$CH$_2$CH$_2$—", where R is as defined above. Alternatively, the end-capping group can also advantageously comprise a detectable label. When the polymer has an end-capping group comprising a detectable label, the amount or location of the polymer and/or the moiety (e.g., active agent) to which the polymer is coupled, can be determined by using a suitable detector. Such labels include, without limitation, fluorescers, chemiluminescers, moieties used in enzyme labeling, colorimetric (e.g., dyes), metal ions, radioactive moieties, and the like. The end-capping group can also advantageously comprise a phospholipid. When the polymer has an end-capping group such as a phospholipid, unique properties (such as the ability to form organized structures with similarly end-capped polymers) are imparted to the polymer. Exemplary phospholipids include, without limitation, those selected from the class of phospholipids called phosphatidylcholines. Specific phospholipids include, without limitation, those selected from the group consisting of dilauroylphosphatidylcholine, dioleylphosphatidylcholine, dipalmitoylphosphatidylcholine, disteroylphosphatidylcholine, behenoylphosphatidylcholine, arachidoylphosphatidylcholine, and lecithin.

"Non-naturally occurring" with respect to a polymer of the invention means a polymer that in its entirety is not found in nature. A non-naturally occurring polymer of the invention may however contain one or more subunits or segments of subunits that are naturally occurring, so long as the overall polymer structure is not found in nature.

"Molecular mass" in the context of a water-soluble polymer of the invention, such as PEG, refers to the nominal average molecular mass of a polymer, typically determined by size exclusion chromatography, light scattering techniques, or intrinsic velocity determination in 1,2,4-trichlorobenzene. The polymers of the invention are typically polydisperse, possessing low polydispersity values of less than about 1.20, and more preferably less than 1.10.

The term "reactive" or "activated" refers to a functional group that reacts readily or at a practical rate under conventional conditions of organic synthesis. This is in contrast to those groups that either do not react or require strong catalysts or impractical reaction conditions in order to react (i.e., a "nonreactive" or "inert" group).

"Not readily reactive" or "inert" with reference to a functional group present on a molecule in a reaction mixture, indicates that the group remains largely intact under conditions effective to produce a desired reaction in the reaction mixture.

A "protecting group" is a moiety that prevents or blocks reaction of a particular chemically reactive functional group in a molecule under certain reaction conditions. The protecting group will vary depending upon the type of chemically reactive group being protected as well as the reaction conditions to be employed and the presence of additional reactive or protecting groups in the molecule. Functional groups which may be protected include, by way of example, carboxylic acid groups, amino groups, hydroxyl groups, thiol groups, carbonyl groups and the like. Representative protecting groups for carboxylic acids include esters (such as a p-methoxybenzyl ester), amides and hydrazides; for amino groups, carbamates (such as tert-butoxycarbonyl) and amides; for hydroxyl groups, ethers and esters; for thiol groups, thioethers and thioesters; for carbonyl groups, acetals and ketals; and the like. Such protecting groups are well-known to those skilled in the art and are described, for example, in T. W. Greene and G. M. Wuts, *Protecting Groups in Organic Synthesis*, Third Edition, Wiley, New York, 1999, and references cited therein.

A functional group in "protected form" refers to a functional group bearing a protecting group. As used herein, the term "functional group" or any synonym thereof is meant to encompass protected forms thereof.

The term "linker" is used herein to refer to an atom or a collection of atoms optionally used to link interconnecting moieties, such as a polymer segment and an electrophile. The linkers of the invention are generally hydrolytically stable.

A "physiologically cleavable" or "hydrolyzable" or "degradable" bond is a relatively weak bond that reacts with water (i.e., is hydrolyzed) under physiological conditions. The tendency of a bond to hydrolyze in water will depend not only on the general type of linkage connecting two central atoms but also on the substituents attached to these central atoms. Appropriate hydrolytically unstable or weak linkages include but are not limited to carboxylate ester, phosphate ester, anhydrides, acetals, ketals, acyloxyalkyl ether, imines, orthoesters, peptides and oligonucleotides, thioesters, thiolesters, and carbonates.

An "enzymatically degradable linkage" means a linkage that is subject to degradation by one or more enzymes.

A "hydrolytically stable" linkage or linker, for the purposes of the present invention, and in particular in reference to the polymers of the invention, refers to an atom or to a collection of atoms, that is hydrolytically stable under normal physiological conditions. That is to say, a hydrolytically stable linkage does not undergo hydrolysis under physiological conditions to any appreciable extent over an extended period of time. Examples of hydrolytically stable linkages include but are not limited to the following: carbon-carbon bonds (e.g., in aliphatic chains), ethers, amides, urethanes, amines, and the like. Hydrolysis rates of representative chemical bonds can be found in most standard chemistry textbooks.

"Branched" in reference to the geometry or overall structure of a polymer refers to polymer having 2 or more polymer "arms". A branched polymer may possess 2 polymer arms, 3 polymer arms, 4 polymer arms, 6 polymer arms, 8 polymer arms or more. One particular type of highly branched polymer is a dendritic polymer or dendrimer, that for the purposes of the invention, is considered to possess a structure distinct from that of a branched polymer.

"Branch point" refers to a bifurcation point comprising one or more atoms at which a polymer splits or branches from a linear structure into one or more additional polymer arms.

A "dendrimer" is a globular, size monodisperse polymer in which all bonds emerge radially from a central focal point or core with a regular branching pattern and with repeat units that each contribute a branch point. Dendrimers exhibit certain dendritic state properties such as core encapsulation, making them unique from other types of polymers.

"Substantially" or "essentially" means nearly totally or completely, for instance, 95% or greater of some given quantity.

An "alkyl" or "alkylene" group, depending upon its position in a molecule and the number of points of attachment of the group to atoms other than hydrogen, refers to a hydrocarbon chain or moiety, typically ranging from about 1 to 20 atoms in length. Such hydrocarbon chains are preferably but not necessarily saturated unless so indicated and may be branched or straight chain, although typically straight chain is preferred. Exemplary alkyl groups include methyl, ethyl, propyl, butyl, pentyl, 1-methylbutyl, 1-ethylpropyl, 3-methylpentyl, and the like.

"Lower alkyl" or "lower alkylene" refers to an alkyl or alkylene group as defined above containing from 1 to 6 carbon atoms, and may be straight chain or branched, as exemplified by methyl, ethyl, n-butyl, i-butyl, t-butyl.

"Cycloalkyl" or "cycloalkylene", depending upon its position in a molecule and the number of points of attachment to atoms other than hydrogen, refers to a saturated or unsaturated cyclic hydrocarbon chain, including polycyclics such as bridged, fused, or spiro cyclic compounds, preferably made up of 3 to about 12 carbon atoms, more preferably 3 to about 8.

"Lower cycloalkyl" or "lower cycloalkylene" refers to a cycloalkyl group containing from 1 to 6 carbon atoms.

"Alicyclic" refers to any aliphatic compound that contains a ring of carbon atoms. An alicyclic group is one that contains a "cycloalkyl" or "cycloalkylene" group as defined above that is substituted with one or more alkyl or alkylenes.

"Non-interfering substituents" are those groups that, when present in a molecule, are typically non-reactive with other functional groups contained within the molecule.

The term "substituted" as in, for example, "substituted alkyl," refers to a moiety (e.g., an alkyl group) substituted with one or more non-interfering substituents, such as, but not limited to: $C_3$-$C_8$ cycloalkyl, e.g., cyclopropyl, cyclobutyl, and the like; halo, e.g., fluoro, chloro, bromo, and iodo; cyano; alkoxy, lower phenyl; substituted phenyl; and the like. For substitutions on a phenyl ring, the substituents may be in any orientation (i.e., ortho, meta, or para).

"Alkoxy" refers to an —O—R group, wherein R is alkyl or substituted alkyl, preferably $C_1$-$C_{20}$ alkyl (e.g., methoxy, ethoxy, propyloxy, benzyl, etc.), preferably $C_1$-$C_7$.

As used herein, "alkenyl" refers to a branched or unbranched hydrocarbon group of 1 to 15 atoms in length, containing at least one double bond, such as ethenyl, n-propenyl, isopropenyl, n-butenyl, isobutenyl, octenyl, decenyl, tetradecenyl, and the like.

The term "alkynyl" as used herein refers to a branched or unbranched hydrocarbon group of 2 to 15 atoms in length, containing at least one triple bond, ethynyl, n-propynyl, isopropynyl, n-butynyl, isobutynyl, octynyl, decynyl, and so forth.

"Aryl" means one or more aromatic rings, each of 5 or 6 core carbon atoms. Aryl includes multiple aryl rings that may be fused, as in naphthyl or unfused, as in biphenyl. Aryl rings may also be fused or unfused with one or more cyclic hydrocarbon, heteroaryl, or heterocyclic rings. As used herein, "aryl" includes heteroaryl.

"Heteroaryl" is an aryl group containing from one to four heteroatoms, preferably N, O, or S, or a combination thereof. Heteroaryl rings may also be fused with one or more cyclic hydrocarbon, heterocyclic, aryl, or heteroaryl rings.

"Heterocycle" or "heterocyclic" means one or more rings of 5-12 atoms, preferably 5-7 atoms, with or without unsaturation or aromatic character and having at least one ring atom which is not a carbon. Preferred heteroatoms include sulfur, oxygen, and nitrogen.

"Substituted heteroaryl" is heteroaryl having one or more non-interfering groups as substituents.

"Substituted heterocycle" is a heterocycle having one or more side chains formed from non-interfering substituents.

"Electrophile" refers to an ion, atom, or collection of atoms that may be ionic, having an electrophilic center, i.e., a center that is electron seeking, capable of reacting with a nucleophile.

"Nucleophile" refers to an ion or atom or collection of atoms that may be ionic, having a nucleophilic center, i.e., a center that is seeking an electrophilic center, and capable of reacting with an electrophile.

"Active agent" as used herein includes any agent, drug, compound, composition of matter or mixture which provides some pharmacologic, often beneficial, effect that can be demonstrated in-vivo or in vitro. This includes foods, food supplements, nutrients, nutriceuticals, drugs, vaccines, antibodies, vitamins, and other beneficial agents. As used herein, these terms further include any physiologically or pharmacologically active substance that produces a localized or systemic effect in a patient.

"Pharmaceutically acceptable excipient" or "pharmaceutically acceptable carrier" refers to an excipient that can be included in the compositions of the invention and that causes no significant adverse toxicological effects to the patient.

"Pharmacologically effective amount," "physiologically effective amount," and "therapeutically effective amount" are used interchangeably herein to mean the amount of a PEG-active agent conjugate present in a pharmaceutical preparation that is needed to provide a desired level of active agent and/or conjugate in the bloodstream or in the target tissue. The precise amount will depend upon numerous factors, e.g., the particular active agent, the components and physical characteristics of pharmaceutical preparation, intended patient population, patient considerations, and the like, and can readily be determined by one skilled in the art, based upon the information provided herein and available in the relevant literature.

"Multi-functional" in the context of a polymer of the invention means a polymer backbone having 3 or more functional groups contained therein, where the functional groups may be the same or different, and are typically present on the polymer termini. Multi-functional polymers of the invention will typically contain from about 3-100 functional groups, or from 3-50 functional groups, or from 3-25 functional groups, or from 3-15 functional groups, or from 3 to 10 functional groups, or will contain 3, 4, 5, 6, 7, 8, 9 or 10 functional groups within the polymer backbone.

A "difunctional" polymer means a polymer having two functional groups contained therein, typically at the polymer termini. When the functional groups are the same, the polymer is said to be homodifunctional. When the functional groups are different, the polymer is said to be heterobifunctional A basic or acidic reactant described herein includes neutral, charged, and any corresponding salt forms thereof.

"Polyolefinic alcohol" refers to a polymer comprising an olefin polymer backbone, such as polyethylene, having multiple pendant hydroxyl groups attached to the polymer backbone. An exemplary polyolefinic alcohol is polyvinyl alcohol.

As used herein, "non-peptidic" refers to a polymer backbone substantially free of peptide linkages. However, the polymer may include a minor number of peptide linkages spaced along the repeat monomer subunits, such as, for example, no more than about 1 peptide linkage per about 50 monomer units.

The term "patient," refers to a living organism suffering from or prone to a condition that can be prevented or treated by administration of a polymer of the invention, typically but not necessarily in the form of a polymer-active agent conjugate, and includes both humans and animals.

"Optional" or "optionally" means that the subsequently described circumstance may or may not occur, so that the description includes instances where the circumstance occurs and instances where it does not.

By "residue" is meant the portion of a molecule remaining after reaction with one or more molecules. For example, a biologically active molecule residue in a polymer conjugate of the invention typically corresponds to the portion of the biologically active molecule up to but excluding the covalent linkage resulting from reaction of a reactive group on the biologically active molecule with a reactive group on a polymer reagent. The term "conjugate" is intended to refer to the entity formed as a result of covalent attachment of a molecule, e.g., a biologically active molecule or any reactive surface, to a reactive polymer molecule, preferably a reactive poly(ethylene glycol).

"Cysteamine" refers to 2-aminoethanethiol, or $H_2N-(CH_2)_2-SH$.

"Cystamine" refers to 2,2'-dithiobis(ethylamine) or $(H_2N-(CH_2)_2-S-)_2$.

Method for Preparing Thiol-Selective Derivatives of Water Soluble Polymers

Overview of the Method

The present invention provides a method for preparing water-soluble polymer derivatives suitable for reaction with thiol groups on proteins or on other active agents. In the method, a water soluble polymer segment having at least one reactive electrophilic terminus is reacted with a bifunctional reactant molecule (that is to say, a reactant molecule possessing at least two functional groups as described below) that contains both a nucleophile (for reaction with the electrophilic terminus of the polymer) and a thiol-selective moiety. Representative thiol selective moieties include thiol, protected thiol, disulfide, maleimide, organomercurials, alpha-haloacetyl compounds such as iodoacetamide, vinyl sulfones, aryl halides, diazoacetates, and orthopyridyl disulfide. The reaction is carried out under conditions effective to promote reaction between the electrophilic terminus of the polymer and the nucleophilic group of the reactant molecule, to form a covalent attachment between the polymer and the reactant molecule. The reaction results in the formation of an activated polymer having a terminus that is selective for reaction with a thiol (e.g., thiol, protected thiol, disulfide, maleimide, vinyl sulfone, iodoacetamide or orthopyridyl disulfide), depending upon the particular reactant molecule employed. A generalized reaction scheme is presented below.

1. Generalized Reaction Scheme

POLY—$L_{0,1}$-E + NU—Y—S ⟶

"POLY - E"   molecular reactant
where "S" is a thiol selective group

-continued

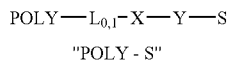

"POLY - S"

2. Exemplary Specific Embodiment

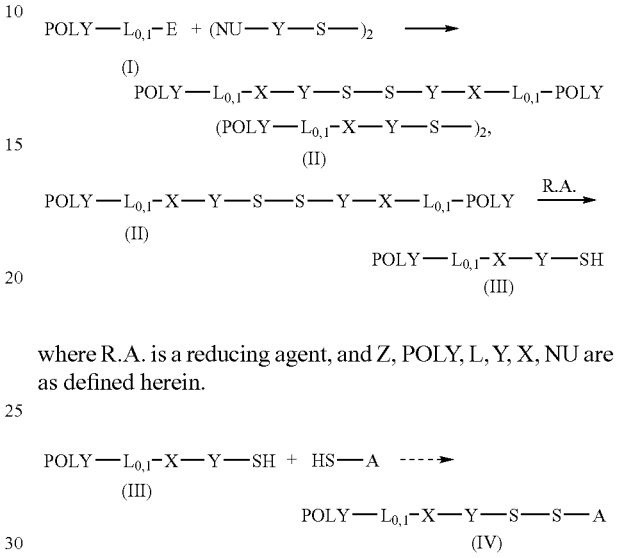

where R.A. is a reducing agent, and Z, POLY, L, Y, X, NU are as defined herein.

POLY—$L_{0,1}$-X—Y—SH + HS—A ----▶
(III)

POLY—$L_{0,1}$-X—Y—S—S—A
(IV)

where A is an active agent.

In its most simplified form, the method can provide activated polyethylene glycol derivatives having a thiol-selective terminus (e.g., a thiol, protected thiol, or maleimide) in one reaction step. In instances in which the reactant molecule possesses a nucleophile that competes with the thiol-selective moiety for reaction with the electrophilic terminus of the polymer, for example when the nucleophile is an amino group and the sulfur containing moiety is a thiol or a thiolate, such as in the exemplary reactant, cysteamine, protection of the thiol group on the reactant molecule may be necessary to prevent reaction of the polymer at the thiol-center of the reactant. Alternatively, if the rates of reaction of the two competing moieties are significantly different, the reaction may be carried out under conditions where the nucleophilic center of the reactant molecule is selectively or preferentially reacted with the electrophile of the polymer. Undesired reaction products resulting from the reaction between the thiol or thiolate and the given electrophile can then be removed by additional purification/separation steps.

A detailed description regarding suitable electrophilically activated polymers and molecular reactants is provided in the sections that follow.

In one preferred embodiment, the reactant molecule is a symmetrical disulfide having two identical nucleophilic groups for reaction with the electrophilic group of the polymer. This approach is advantageous because no competition exists between potentially different nucleophiles in the reactant molecule. Thus, under suitable reaction conditions (e.g., when an at least a two fold molar excess of electrophilically activated polymer is employed—sufficient to react with all of the nucleophile groups in the symmetrical disulfide), only one activated polymer product is formed.

Exemplary symmetrical reactant molecules will possess a central disulfide (—S—S—) bond where the sulfur atoms are each connected to identical Y groups such as alkylene, substituted alkylene, cycloalkylene, substituted cycloalkylene, aryl, or substituted aryl group possessing a nucleophile (NU) such as an amino, hydroxy, thiol, imino, thioester or the like covalently attached thereto, "(NU-Y—S)$_2$". One such preferred symmetrical reactant molecule is cystamine. Reaction of an electrophilically activated polymer with a symmetrical disulfide reagent such as cystamine results in formation of a symmetrical disulfide polymer having identical polymer segments extending from each of the sulfur atoms of a central disulfide linkage. Illustrative reactions carried out with different electrophilically activated polymers and the reactant, cystamine, are provided in the Examples (Examples 1-3). The electrophilically-activated polymer is typically reacted with a bi-functional reactant molecule under very mild reaction conditions (e.g., room temperature), offering another advantage of this approach. Moreover, typical yields are greater than 70%, preferably greater than 80%, more preferably greater than 90%, and often even greater than 95%.

Due to the symmetry of the resulting disulfide polymer, cleavage by action of a reducing agent such as dithiothreitol results in formation of two moles of the corresponding thiol-selective polymer derivative ("POLY-S").

Preferred polymers (POLY-E's) for use in the present invention include methoxy-PEG propanoic acid and methoxy-PEG butanoic acid and activated forms thereof. Particularly preferred polymer derivatives having a thiol selective terminus are provided in structures (11), (13), and (18) described herein.

In another preferred embodiment, the polymer derivatives of the invention are prepared from polymer acid or polymer acid-equivalent starting materials, where the polymer acid is purified prior to the reaction with the nucleophile. A polymer acid or polymer acid equivalent is a water soluble polymer of the invention having at least one functional group or terminus that is a carboxylic acid or a carboxylic acid-equivalent such as an activated derivative of a carboxylic acid. The use or preparation of a polymer acid provides an additional advantage in that it allows for the ready removal of PEG diol or PEG diol-derived impurities that may be present in the polymer starting material, depending upon its source.

Often, polyethylene glycol starting materials, such as electrophilically activated PEG, as used in many embodiments of the invention, contain detectable amounts of PEG diol impurity, often ranging from 0.5% to over 30% by weight. Any amount of diol impurity can be a problem, since the diol (and its reaction products) can be extremely difficult to remove/separate. Additionally, due to its reactivity, PEG-diol (and more particularly its conversion products) can react with a bioactive agent during a coupling reaction, resulting in the formation of a mixture of conjugate products. The resulting mixture of conjugates can be difficult to analyze, i.e., to determine the extent of diol-derived impurities present. Moreover, separation of the desired conjugate product from the diol-derived conjugate products can be extremely difficult, and in some instances, may be impossible to achieve. In particular, high molecular weight water soluble polymers such as methoxy-PEG-OH (e.g., having a molecular weight of greater than about 30,000 daltons) can contain up to 30 percent by weight or more diol, depending upon the source and/or the method of making the PEG starting material. As discussed above, such diol and diol-derived impurities can be especially problematic when carried through a series of synthetic transformations and/or a conjugation reaction. The use of a polymer acid, such as in method of the invention, allows for the purification, e.g., by chromatography, of the POLY-E starting material (or its equivalent precursor) and the ultimate formation of a thiol-selective polymer formulation that is essentially free of reactive PEG-diol or reactive PEG-diol derived impurities.

The applicants have recognized that separation of PEG-diol-related impurities at the front end of a reaction or series of reactions leading to the formation of a reactive polymer derivative or eventually a polymer conjugate is advantageous, since separation/purification at this stage is more readily accomplished when compared to the separation of various polymer conjugate species.

Alternatively, as an approach for removing or rendering inert mPEG-diol derived impurities, the water-soluble polymer provided in step (i), POLY-E, may be prepared from a diol-free PEG-OH prepared from benzyloxy-PEG as described in co-owned U.S. Pat. No. 6,448,369. In this approach, the benzyloxy-PEG-OH starting material is prepared preferentially by polymerization of ethylene oxide onto the benzyloxide ion, Bz-O$^-$, resulting in high purity monofunctional benzyloxy PEGs containing PEG-diol. After converting all PEG-OH groups to inert methyl ethers and removing benzyloxy groups in subsequent steps, the method provides pure, diol-free methoxy-PEG-OH. In utilizing this method, PEG-diol is converted to its non-reactive ether form, rendering it an inert component of the resulting composition.

In sum, the method provided herein (i) avoids multiple cumbersome reaction steps, (ii) does not necessarily require multiple protecting/deprotecting steps, (iii) is carried out under mild conditions such that the polymer segment is not particularly susceptible to damage, (iv) results in a high yields of product, typically greater than 90%, and (v) provides a new class of polymer derivatives having a thiol-selective terminus. The overall synthetic methodology, reagents, polymer derivatives, compositions, and conjugates of the invention will now be described more fully below.

Polymer Reactants, POLY-L$_{0,1}$-E

The Polymer Segment, POLY

The following describes the polymer segment designated herein as POLY, applicable to the electrophilically activated polymers of the method, as well as the thiol-selective polymers of the invention. Electrophilically-activated polymer derivatives useful in the present invention generally comprise at least one electrophile coupled to a water soluble polymer segment. The electrophile can either be covalently bonded directly to the polymer segment, or alternatively can be coupled to the polymer backbone via a linking group, L.

Representative POLYs include poly(alkylene glycols) such as poly(ethylene glycol), poly(propylene glycol) ("PPG"), copolymers of ethylene glycol and propylene glycol, poly(olefinic alcohol), poly(vinylpyrrolidone), poly(hydroxyalkylmethacrylamide), poly(hydroxyalkylmethacrylate), poly(saccharides), poly(a-hydroxy acid), poly(vinyl alcohol), polyphosphazene, polyoxazoline, and poly(N-acryloylmorpholine). POLY can be a homopolymer, an alternating copolymer, a random copolymer, a block copolymer, an alternating tripolymer, a random tripolymer, or a block tripolymer of any of the above. The water-soluble polymer segment is preferably, although not necessarily, a poly(ethylene glycol) "PEG" or a derivative thereof.

The polymer segment can have any of a number of different geometries, for example, POLY can be linear, branched, or forked. Most typically, POLY is linear or is branched, for example, having 2 polymer arms. Although much of the discussion herein is focused upon PEG as an illustrative POLY, the discussion and structures presented herein can be readily extended to encompass any of the water-soluble polymer segments described above.

Any water-soluble polymer having at least one electrophilically activated terminus can be used to prepare a thiol-selective polymer in accordance with the method of the invention. Although water-soluble polymers bearing only a single reactive electrophilically activated terminus are typically used and illustrated herein, polymers bearing two, three, four, five, six, seven, eight, nine, ten, eleven, twelve or more reactive termini suitable for conversion to a thiol selective polymer as set forth herein can be used. Advantageously, as the number of hydroxyl or other reactive moieties on the water-polymer segment increases, the number of available sites for introducing an electrophilic group increases. Non-limiting examples of the upper limit of the number of hydroxyl and/or electrophilic moieties associated with the water-soluble polymer segment include from about 1 to about 500, from 1 to about 100, from about 1 to about 80, from about 1 to about 40, from about 1 to about 20, and from about 1 to about 10.

In turning now to the preferred POLY, PEG encompasses poly(ethylene glycol) in any of its linear, branched or multi-arm forms, including end-capped PEG, forked PEG, branched PEG, pendant PEG, and PEG containing one or more degradable linkage separating the monomer subunits, to be more fully described below.

A PEG polymer segment comprises the following: —(CH$_2$CH$_2$O)$_n$—CH$_2$CH$_2$—, where (n) typically ranges from about 3 to about 4,000, or from about 3 to about 3,000, or more preferably from about 20 to about 1,000.

POLY can be end-capped, where PEG is terminally capped with an inert end-capping group. Preferred end-capped PEGs are those having as an end-capping moiety such as alkoxy, substituted alkoxy, alkenyloxy, substituted alkenyloxy, alkynyloxy, substituted alkynyloxy, aryloxy, substituted aryloxy. Preferred end-capping groups are C$_1$-C$_{20}$ alkoxy such as methoxy, ethoxy, and benzyloxy. The end-capping group can also advantageously comprise a phospholipid. Exemplary phospholipids include phosphatidylcholines, such as dilauroylphosphatidylcholine, dioleylphosphatidylcholine, dipalmitoylphosphatidylcholine, disteroylphosphatidylcholine, behenoylphosphatidylcholine, arachidoylphosphatidylcholine, and lecithin.

Referring now to any of the structures comprising a polymer segment, POLY, POLY may correspond or comprise the following:

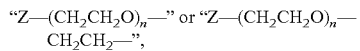

where n ranges from about 3 to about 4000, or from about 10 to about 4000, and Z is or includes a functional group, which may be a reactive group or an end-capping group. Examples of Z include hydroxy, amino, ester, carbonate, aldehyde, acetal, aldehyde hydrate, ketone, ketal, ketone hydrate, alkenyl, acrylate, methacrylate, acrylamide, sulfone, thiol, carboxylic acid, isocyanate, isothiocyanate, hydrazide, urea, maleimide, vinylsulfone, dithiopyridine, vinylpyridine, iodoacetamide, alkoxy, benzyloxy, silane, lipid, phospholipid, biotin, and fluorescein, including activated and protected forms thereof where applicable. Preferred are functional groups such as N-hydroxysuccinimidyl ester, 1-hydroxybenzotriazolyl carbonate, amine, vinylsulfone, maleimide, N-succinimidyl carbonate, hydrazide, succinimidyl propionate, succinimidyl butanoate, succinimidyl succinate, succinimidyl ester, glycidyl ether, oxycarbonylimidazole, p-nitrophenyl carbonate, aldehyde, orthopyridyl-disulfide, and acrylol.

The polymer reactant (and corresponding product) may possess a dumbbell-like or bifunctional linear structure, e.g., in which two electrophiles are interconnected by a central POLY, e.g., PEG. More specifically, such POLY may be represented by the structure E1-PEG-E2, where E1 and E2 are independently selected electrophiles as described herein. Preferably, E1 and E2 are the same. Exemplary PEGs falling into this classification are provided in Example 3, e.g., (15) and (16). Additional examples are provided in U.S. Pat. No. 5,900,461, the content of which is expressly incorporated herein by reference. In a preferred embodiment, particularly in regard to the thiol-selective polymers of the invention, or their precursors, the functional group, Z, may correspond to "L$_{0,1}$-X—Y—S" to provide a homo-bifunctional thiol-selective polymer having identical groups on either side of the polymer segment, e.g., S—Y—X-L$_{0,1}$-POLY-L$_{0,1}$-X—Y—S, VIII.

These and other functional groups, Z, are described in the following references, all of which are incorporated by reference herein: N-succinimidyl carbonate (see e.g., U.S. Pat. Nos. 5,281,698, 5,468,478), amine (see, e.g., Buckmann et al. Makromol. Chem. 182:1379 (1981), Zalipsky et al. Eur. Polym. J. 19:1177 (1983)), hydrazide (See, e.g., Andresz et al. Makromol. Chem. 179:301 (1978)), succinimidyl propionate and succinimidyl butanoate (see, e.g., Olson et al. in Poly(ethylene glycol) Chemistry & Biological Applications, pp 170-181, Harris & Zalipsky Eds., ACS, Washington, D.C., 1997; see also U.S. Pat. No. 5,672,662), succinimidyl succinate (See, e.g., Abuchowski et al. Cancer Biochem. Biophys. 7:175 (1984) and Joppich et al., Makromol. Chem. 180:1381 (1979), succinimidyl ester (see, e.g., U.S. Pat. No. 4,670, 417), benzotriazole carbonate (see, e.g., U.S. Pat. No. 5,650, 234), glycidyl ether (see, e.g., Pitha et al. Eur. J. Biochem. 94:11 (1979), Elling et al., Biotech. Appl. Biochem. 13:354 (1991), oxycarbonylimidazole (see, e.g., Beauchamp, et al., Anal. Biochem. 131:25 (1983), Tondelli et al. J. Controlled Release 1:251 (1985)), p-nitrophenyl carbonate (see, e.g., Veronese, et al., Appl. Biochem. Biotech., 11:141 (1985); and Sartore et al., Appl. Biochem. Biotech., 27:45 (1991)), aldehyde (see, e.g., Harris et al. J. Polym. Sci. Chem. Ed. 22:341 (1984), U.S. Pat. Nos. 5,824,784, 5,252,714), maleimide (see, e.g., Goodson et al. Bio/Technology 8:343 (1990), Romani et al. in Chemistry of Peptides and Proteins 2:29 (1984)), and Kogan, Synthetic Comm. 22:2417 (1992)), orthopyridyl-disulfide (see, e.g., Woghiren, et al. Bioconj. Chem. 4:314 (1993)), acrylol (see, e.g., Sawhney et al., Macromolecules, 26:581 (1993)), vinylsulfone (see, e.g., U.S. Pat. No. 5,900,461).

Again, the POLY types described are meant to encompass linear polymer segments, and also branched or forked polymer segments. In an instance where the polymer segment is branched, the POLY structure may, for example, correspond to the polymer arms forming part of the overall POLY structure. Alternatively, in an instance where POLY possesses a forked structure, POLY may, for example, correspond to the linear portion of the polymer segment prior to the branch point.

POLY also encompasses branched PEG molecules having 2 arms, 3 arms, 4 arms, 5 arms, 6 arms, 7 arms, 8 arms or more. Branched polymers used to prepare the thiol-selective polymers of the invention may possess anywhere from 2 to 300 or so reactive termini. Preferred are branched polymer segments having 2 or 3 polymer arms. An illustrative branched POLY, as described in U.S. Pat. No. 5,932,462, corresponds to the structure:

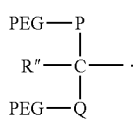

In this representation, R" is a nonreactive moiety, such as H, methyl or a PEG, and P and Q are non-reactive linkages. In a preferred embodiment, the branched PEG polymer segment is methoxy poly(ethylene glycol) disubstituted lysine.

In the above particular branched configuration, the branched polymer segment possesses a single reactive site extending from the "C" branch point for positioning of the reactive electrophilic group of the polymer reactant or the X group of the thiol-selective polymer product. Branched PEGs such as these for use in the present invention will typically have fewer than 4 PEG arms, and more preferably, will have 2 or 3 PEG arms. Such branched PEGs offer the advantage of having a single reactive site, coupled with a larger, more dense polymer cloud than their linear PEG counterparts. Illustrative branched polymers bearing electrophilic groups such as these are commercially available from Nektar (Huntsville, Ala.), and include mPEG2-N-hydroxysuccinimide.

An illustrative branched polymer reactant and corresponding thiol-selective polymer of the invention, respectively, have the structures shown below:

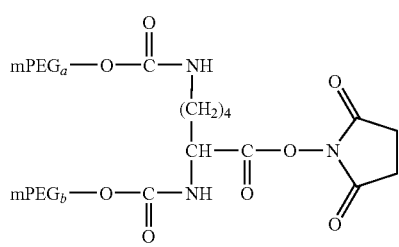

IX-A

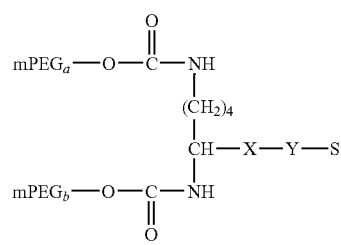

IX-B where X, Y, and S are as described herein. In structure IX-B, X may correspond to —C(O)-G, where G is —NH.

Branched polymers for use in preparing a polymer of the invention additionally include those represented more generally by the formula R(POLY)$_n$, where R is a central or core molecule from which extends 2 or more POLY arms such as PEG. The variable n represents the number of POLY arms, where each of the polymer arms can independently be end-capped or alternatively, possess a reactive functional group at its terminus. Typically, at least one polymer arm possesses a terminal functional group. In such multi-armed embodiments of the invention, each PEG arm typically possesses an electrophile at its terminus (or the corresponding reaction product between the electrophile and the nucleophile as previously described). Branched PEGs such as those represented generally by the formula, R(PEG)$_n$, above possess 2 polymer arms to about 300 polymer arms (i.e., n ranges from 2 to about 300). Preferably, such branched PEGs possess from 2 to about 25 polymer arms, more preferably from 2 to about 20 polymer arms, and even more preferably from 2 to about 15 polymer arms or fewer. Most preferred are multi-armed polymers having 3, 4, 5, 6, 7 or 8 arms.

Preferred core molecules in branched PEGs as described above are polyols. Such polyols include aliphatic polyols having from 1 to 10 carbon atoms and from 1 to 10 hydroxyl groups, including ethylene glycol, alkane diols, alkyl glycols, alkylidene alkyl diols, alkyl cycloalkane diols, 1,5-decalin-diol, 4,8-bis(hydroxymethyl)tricyclodecane, cycloalkylidene diols, dihydroxyalkanes, trihydroxyalkanes, and the like. Cycloaliphatic polyols may also be employed, including straight chained or closed-ring sugars and sugar alcohols, such as mannitol, sorbitol, inositol, xylitol, quebrachitol, threitol, arabitol, erythritol, adonitol, ducitol, facose, ribose, arabinose, xylose, lyxose, rhamnose, galactose, glucose, fructose, sorbose, mannose, pyranose, altrose, talose, tagitose, pyranosides, sucrose, lactose, maltose, and the like. Additional aliphatic polyols include derivatives of glyceraldehyde, glucose, ribose, mannose, galactose, and related stereoisomers. Other core polyols that may be used include crown ether, cyclodextrins, dextrins and other carbohydrates such as starches and amylose. Preferred polyols include glycerol, pentaerythritol, sorbitol, and trimethylolpropane.

A representative multi-arm structure corresponding to a thiol-selective polymer of the invention is shown below, where n preferably ranges from about 3 to about 8.

$$R-(POLY-L_{0,1}-X-Y-S)_n \qquad X$$

Additional multi-arm polymers for use in preparing a thiol-selective polymer of the invention include multi-arm PEGs available from Nektar (Huntsville, Ala.). Preferred multi-armed electrophilically activated polymers for use in the method of the invention correspond to the following structure, where E represents an electrophilic group,

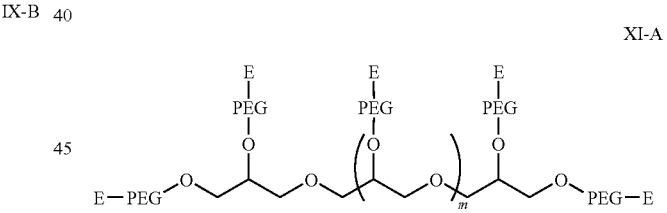

XI-A

PEG is —(CH$_2$CH$_2$O)$_n$CH$_2$CH$_2$—, and m is selected from the group consisting of 3, 4, 5, 6, 7, and 8. Of course, the corresponding thiol-selective polymer product possesses the structure shown above with the exception that the electrophile, E, is replaced by "—X—Y—S" (XI-B).

Alternatively, the polymer segment may possess an overall forked structure. An example of a forked PEG corresponds to the following generalized structure, where the first structure represents an electrophilically activated forked PEG and the second structure represents a forked thiol-selective polymer product:

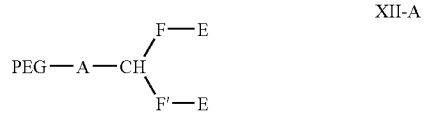

XII-A

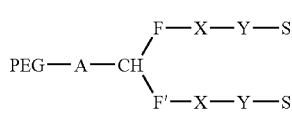

XII-B where PEG is any of the forms of PEG described herein, A is a linking group, preferably a hydrolytically stable linkage such as oxygen, sulfur, or —C(O)—NH—, F and F' are hydrolytically stable spacer groups that are optionally present, and the other variables corresponding to E, X, Y, and S are as defined above. Both the general and specific descriptions of possible values for X, Y and S are applicable to the structure above. Examplary linkers and spacer groups corresponding to A, F and F' are described in International Application No. PCT/US99/05333, and are useful in forming polymer segments of this type for use in the present invention. F and F' are spacer groups that may be the same of different. In one particular embodiment of the above, PEG is MPEG, A corresponds to —C(O)—NH—, and F and F' are both methylene or —$CH_2$—. This type of polymer segment is useful for reaction with two active agents, where the two active agents are positioned a precise or predetermined distance apart, depending upon the selection of F and F'.

In any of the representative structures provided herein, one or more degradable linkages may be contained in the polymer segment to allow generation in vivo of a PEG-disulfide linked conjugate having a smaller PEG chain than in the initially administered conjugate. Appropriate physiologically cleavable linkages include but are not limited to ester, carbonate ester, carbamate, sulfate, phosphate, acyloxyalkyl ether, acetal, and ketal. Such linkages when contained in a given polymer segment will preferably be stable upon storage and upon initial administration. More particularly, as described generally above, two or more polymer segments connected by a hydrolyzable linkage may be represented by the following structure: PEG1-W-PEG2 (where PEG1 and PEG2 can be the same or different) and W represents a weak, hydrolyzable linkage. These polymer structures contain PEG arms or portions of PEG arms that are removable (i.e., cleavable) in-vivo.

Additional representative PEGs having either linear or branched structures for use in preparing the conjugates of the invention may be purchased from Nektar Therapeutics (formerly Shearwater Corporation, Huntsville, Ala.). Illustrative structures are described in Shearwater's 2001 catalogue entitled "Polyethylene Glycol and Derivatives for Biomedical Applications", the contents of which is expressly incorporated herein by reference.

Generally, the nominal average molecular mass of the water-soluble polymer segment, POLY will vary. The nominal average molecular mass of POLY typically falls in one or more of the following ranges: about 100 daltons to about 100,000 daltons; from about 500 daltons to about 80,000 daltons; from about 1,000 daltons to about 50,000 daltons; from about 2,000 daltons to about 25,000 daltons; from about 5,000 daltons to about 20,000 daltons. Exemplary nominal average molecular masses for the water-soluble polymer segment POLY include about 1,000 daltons, about 5,000 daltons, about 10,000 daltons, about 15,000 daltons, about 20,000 daltons, about 25,000 daltons, about 30,000 daltons, and about 40,000 daltons. Low molecular weight POLYs possess molecular masses of about 250, 500, 750, 1000, 2000, or 5000 daltons. Exemplary thiol selective derivatives comprise PEGs having a molecular weight selected from the group consisting of 5,000 daltons, 20,000 daltons and 40,000 daltons as provided in Examples 1-3.

In one particular embodiment of the invention, an activated thiol selective derivative as provided herein possesses a PEG segment having one of the following nominal average molecular masses: 500, 1000, 2000, 3000, 5000, 10,000, 15,000, 20,000, 30,000 and 40,000 daltons.

In terms of the number of subunits, PEGs for use in the invention will typically comprise a number of (—$OCH_2CH_2$—) subunits falling within one or more of the following ranges: 10 to about 4000 subunits, from about 20 to about 1000 subunits, from about 25 to about 750 subunits, from about 30 to about 500 subunits.

Although any of a number of polymers (POLY) may be utilized, in one embodiment, the polymer comprises a hydrophilic polymer, that is to say, a polymer containing fewer than about 25 subunits of polypropylene oxide or other similar hydrophobic polymer segments. The polymer may, in an alternative embodiment, be absent polypropylene oxide or similar hydrophobic subunits. In one instance, the polymer is preferably not a pluronic-type polymer. In yet another particular embodiment, the polymer is preferably not bound to a solid support. In yet another specific instance, a polymer of the invention is one that may be although is not necessarily substantially absent fatty acid groups or other lipophilic moieties.

Polymer Electrophilic Groups ("E")

A polymer for use in the method contains as least one electrophile or electrophilic group (-E) suitable for reaction with a nucleophile, such as that contained in the thiol-selective reactant molecule. Exemplary electrophiles include activated esters (e.g. N-hydroxysuccinimidyl (NHS) ester or 1-hydroxybenzotriazolyl ester), active carbonates (e.g. N-hydroxysuccinimidyl carbonate, para-nitrophenylcarbonate, and 1-hydroxybenzotriazolyl carbonate), acetal, aldehyde, aldehyde hydrate, active anhydrides such as acid anhydrides, acid halide, aryl halide, ketone, carboxylic acid, isocyanate, isothiocyanate, imidoester, and the like. Particularly preferred are activated esters such as NHS esters. In sum, a polymer segment having the generalized structure, POLY-$L_{0,1}$-E, can possess any electrophilic group at at least one terminus, where exemplary electrophiles include those described above.

Polymer Linkers, L

In most cases, the polymer segment is directly attached to the electrophile. Alternatively, the polymer segment is attached to the electrophile via an intervening linker, L. When such a linker is utilized, it is represented generally herein as Li, meaning that such a linker is present. When such a linker is absent, it is represented herein generally as L. Linkers for use in the instant invention are typically $C_1$-$C_{10}$ alkyl or $C_1$-$C_{10}$ substituted alkyl. One particularly preferred linker, e.g., in the instance where the polymer segment is PEG, e.g., —($CH_2CH_2$—O)$_n$—$CH_2CH_2$—, is a methylene group, —$CH_2$—, although any linear lower alkyl, or branched lower alkyl, or their substituted counterparts may similarly be employed.

Purified Electrophilically Activated Polymers

Particular suitable for use in the present method are electrophilically activated PEG reagents such as chromatographically purified carboxylic acids or their functional equivalents, such as mPEG-succinimidyl propionate, mPEG-succinimidyl butanoate, mPEG-CM-HBA-NHS, mPEG2-NHS, and the like available from Nektar, Huntsville, Ala. By virtue of their acid functionality, such electrophilically activated PEGs are more readily purified prior rather than subsequent to reaction with a bifunctional reactant molecule, NU-Y—S, to allow separation of PEG-diol or diol-derived impurities. Purification of POLY-E can be accomplished by any of a number of purification methods commonly employed in the art, although chemical-based separation and chromatographic methods are preferred. One such preferred chromatography method is ion-exchange chromatography or IEC. IEC is useful for the separation of any charged molecule, such as a PEG-acid. Typical ion exchange chromatography conditions can be readily determined by one of skill in the art, such as the particular column, pH range employed, ionic strength, choice of buffer, gradient, and the like.

In some instances, gel permeation chromatography or GPC is utilized to determine the purity of PEG-containing reactants and derivatives. So, in one instance, GPC may be used to determine the extent of PEG-diol or diol-derived impurities in a given PEG-starting material or PEG reactant. Once having confirmed the presence and quantity of PEG-diol, e.g., by GPC, the PEG-starting material or derivative, such as a PEG-acid, is then purified by ion exchange chromatography to remove any PEG-diol or PEG-diol related impurities, such that the resulting PEG composition is substantially absent such bifunctional PEG impurities.

Such electrophilically activated PEG reagents are preferably substantially pure, i.e., absent PEG-diol or reactive difunctional PEG-diol derived impurities. Preferably, the starting material, POLY-L$_{0,1}$-E, will contain less than about 10% of any such impurity, preferably less than about 5% of any such impurity, and more preferably less than about 2% or no detectable amount of any such impurity. Correspondingly, this means that the resulting thiol-specific-functionalized polymer, POLY-S, preferably comprises at least 90% or at least 95% or at least 98% or more of the desired polymer-based product absent significant amounts of difunctionalized polyethylene glycol impurities derived from PEG-diol. Certain difunctionalized polymer impurities of this type, particularly the corresponding dithiols or protected dithiols resulting from carrying through such impurities when practicing the method of the invention, can be very difficult to remove. Such reactive impurities, if carried through the reaction scheme to the final activated polymer derivative, can then react with target coupling moieties such as thiol-containing groups in proteins or other active agents, to provide polymer conjugates in addition to those intended.

Thiol-selective Reactant Molecule

In accordance with the method of the invention, POLY-L$_{0,1}$-E is reacted with a reactant molecule that contains both a nucleophile (-NU) for reaction with the electrophilic group of the activated polymer and a thiol-selective group as described above. Generally, a molecular reactant for use in the invention will possess the structure NU-Y—S where NU is a nucleophile, Y is a group interposed between NU and S, and S is a thiol-selective group.

"Y"

Y is typically but is not necessarily linear in nature. The overall length of the Y group will typically range between 1 to about 20 atoms, or from about 2 to 15 atoms, where by length is meant the number of atoms in a single chain, not counting substituents. For instance, —CH$_2$— counts as one atom with respect to overall linker length, —CH$_2$CH$_2$O— counts as 3 atoms in length. Preferably, Y has a length of about 1 to about 20 atoms, or from about 2 to about 15 atoms, or from about 1 to about 6 atoms, and is hydrolytically stable. Representative Y groups may be any of the following: —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—CH$_2$—, —CH$_2$—O—CH$_2$—CH$_2$—, —CH$_2$—CH$_2$— O—CH$_2$—, —CH$_2$—CH$_2$—CH$_2$—O—, —O—CH$_2$— CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$— O—CH$_2$—, —CH$_2$—CH$_2$—CH$_2$—CH$_2$—O—, —C(O)— NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)— NH—CH$_2$—CH$_2$—, —CH$_2$—CH$_2$—C(O)—NH—CH$_2$—, —CH$_2$—CH$_2$—CH$_2$—C(O)—NH—, —C(O)—NH— CH$_2$—CH$_2$—CH$_2$—CH$_2$—, —CH$_2$—C(O)—NH—CH$_2$— CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$— CH$_2$—CH$_2$—C(O)—NH—CH$_2$—CH$_2$—, —CH$_2$—CH$_2$— CH$_2$—CH$_2$—C(O)—NH—, —C(O)—O—CH$_2$—, —CH$_2$—C(O)—O—CH$_2$—, —CH$_2$—CH$_2$—C(O)—O— CH$_2$—, —C(O)—O—CH$_2$—CH$_2$—, —NH—C(O)— CH$_2$—, —CH$_2$—NH—C(O)—CH$_2$—, —CH$_2$—CH$_2$— NH—C(O)—CH$_2$—, —NH—C(O)—CH$_2$—CH$_2$—, —CH$_2$—NH—C(O)—CH$_2$—CH$_2$, —CH$_2$—CH$_2$—NH—C (O)—CH$_2$—CH$_2$, —C(O)—NH—CH$_2$—, —C(O)—NH— CH$_2$—CH$_2$—, —O—C(O)—NH—CH$_2$—, —O—C(O)— NH—CH$_2$—CH$_2$—, —NH—CH$_2$—, —NH—CH$_2$— CH$_2$—, —CH$_2$—NH—CH$_2$—, —CH$_2$—CH$_2$—NH— CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—CH$_2$—C (O)—, —CH$_2$—CH$_2$—CH$_2$—C(O)—NH—CH$_2$—CH$_2$— NH—, —CH$_2$—CH$_2$—CH$_2$—C(O)—NH—CH$_2$—CH$_2$— NH—C(O)—, —CH$_2$—CH$_2$—CH$_2$—C(O)—NH—CH$_2$— CH$_2$—NH—C(O)—CH$_2$—, a cycloalkylene group, or a substituted cycloalkylene group, —CH$_2$—CH$_2$—CH$_2$—C (O)—NH—CH$_2$—CH$_2$—NH—C(O)—CH$_2$—CH$_2$—, and combinations of two or more of any of the foregoing.

Preferred Y groups for use in the invention include, for example, alkylene, substituted alkylene, cycloalkylene, substituted cycloalkylene, aryl, and substituted aryl. Y typically comprises from about 2 to about 10 carbon atoms, and optionally may contain additional non-interfering atoms. Illustrative Y groups possess the structure:

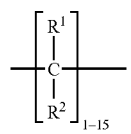

where R$^1$ and R$^2$ in each occurrence are each independently H or an organic radical that is selected from the group consisting of alkyl, substituted alkyl, cycloalkyl, substituted cycloalkyl, alkylenecycloalkyl, cycloalkylene, substituted cycloalkylene, and substituted alkylenecycloalkyl. Preferably, Y is composed of from two to about ten carbon atoms. Exemplary Y groups include methylene (—CH$_2$—), ethylene (—CH$_2$CH$_2$—), propylene (—CH$_2$CH$_2$CH$_2$—), butylene (—CH$_2$CH$_2$CH$_2$CH$_2$—), pentylene (—CH$_2$CH$_2$CH$_2$CH$_2$CH$_2$—), 2-methylpropyl, substituted counterparts, and the like. In a particular embodiment of the above structure, R$^1$ and R$^2$ are both H.

Another preferred Y group possesses the structure: —(CH$_2$)$_{1,2,3,4,5}$—NH—C(O)—CH$_2$CH$_2$—.

Thiol-Selective Group, "S"

Exemplary thiol-selective groups include thiol, protected thiol, disulfide, maleimide, vinylsulfone, iodoacetamide, and orthopyridyl disulfide. "S" as set forth herein represents any thiol-selective group. Particularly, "S" may represent a thiol, thiolate, disulfide or other protected thiol group. Protecting groups for the thiol moiety, besides disulfide, include trityl, thioethers such as alkyl and benzyl thioethers, including monothio, dithio and aminothio acetals, thioesters, thiocarbonates, thiocarbamates, and sulfenyl derivatives. Structures corresponding to these exemplary "S" groups are provided below, where a dotted line indicates a point of attachment to the Y portion of the molecule. A-SH indicates an active agent having a thiol group.

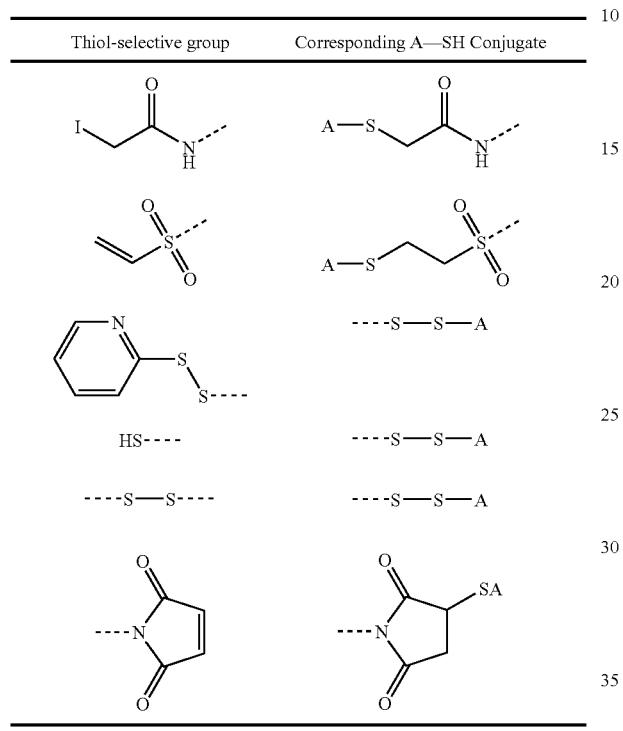

| Thiol-selective group | Corresponding A—SH Conjugate |

The Nucleophile

The nucleophile portion of the reactant molecule is any nucleophile commonly known in the art. Preferred nucleophiles include primary amino, secondary amino, hydroxy, imino, thiol, thioester and the like. Secondary amino groups will typically possess as a substituent a lower alkyl group such as methyl, ethyl.

Thus, molecular reactant molecules for use in the invention possess any combination of NU, Y, and S groups provided herein. Preferred molecular reactants include cystamine, an illustrative symmetrical amino disulfide compound, and cysteamine, an amino thiol, as well as is N-(2-amino-ethyl)-3-maleimido-propionamide. Reactions carried out with the exemplary molecular reactant, cystamine, are provided in Examples 1-3 and an exemplary reaction scheme with the molecular reactant, N-(2-amino-ethyl)-3-maleimido-propionamide, is provided below.

Preparation of a Maleimide from POLY-E, where E is an acid or acid equivalent

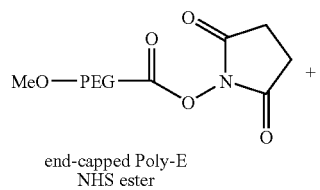

end-capped Poly-E
NHS ester

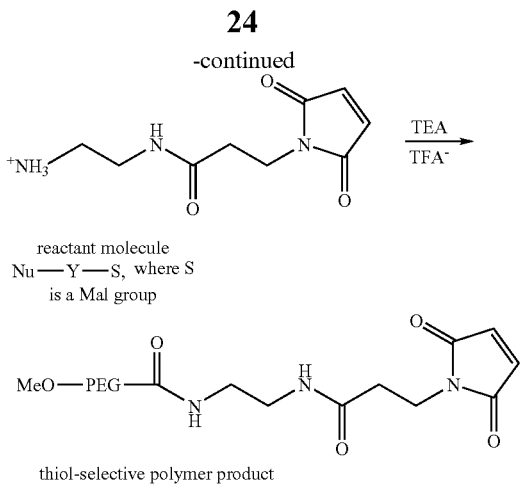

reactant molecule
Nu—Y—S, where S
is a Mal group thiol-selective polymer product Reaction Conditions The reaction between the electrophilic group of the polymer and the nucleophile in the molecular reactant is typically although not necessarily carried out under mild reaction conditions, depending of course on the particular electrophile and nucleophile that are undergoing reaction. Typically, such reactions are conducted at temperatures at around 100° C. or less, or at 65° C. or less, or at 40° C. or less, or at about 25° C. or less. The reacting step is typically carried out in an organic solvent such as acetone, acetonitrile, chlorinated hydrocarbons such as chloroform and dichloromethane, aromatic hydrocarbons such as benzene, toluene or xylene, tetrahydrofuran (THF), dimethylformamide (DMF), or dimethylsulfoxide.

Particular reaction conditions (solvent, molar ratios of reactants, temperature, atmosphere, reaction times) will be readily determined by one skilled in the art, depending upon the choice of particular reactants and the desired products. The course or progress of the reaction can be monitored by any of a number of common analytical techniques such as thin layer chromatography or $^1$H NMR In instances in which the thiol-selective moiety is a protected thiol, an additional deprotection step may be required. Conditions for deprotection will depend upon the nature of the protecting group, and such can readily be determined by one skilled in the art, e.g., as described in Greene, T., and Wuts, Peter G. M., "PROTECTIVE GROUPS IN ORGANIC SYNTHESIS, Chapter 6, $3^{rd}$ Edition, John Wiley and Sons, Inc., New York, 1999 (p. 454-493).

When a symmetrical disulfide reagent such as cystamine is employed as the molecular reactant, the resulting polymer product is a symmetrical polymer having a central disulfide bond. Representative symmetrical water-soluble polymers having a central disulfide bond are provided as structures (10) and (12), although many alternative structures having these basic features may readily be envisioned, based upon the descriptions of the reaction and POLY, $L_1$, E, NU, Y, and S groups provided herein. The symmetrical polymer disulfide can then be converted to the corresponding thiol-terminated polymer, e.g., (11) and (13), and the like, by reduction with a suitable reducing agent such as dithiothreitol, Sn/HCl, Na/xylene, ammonia, lithium aluminum hydride, sodium borohydride or any other reducing agent known in the art.

Thiol-selective Polymers

In another aspect, the invention also provides thiol-selective polymers having the features and components described above. Generally, a thiol-selective polymer of the possesses the following structure: POLY-$L_{0,1}$-X—Y—S, where the variables L, X, Y and S have been previously described. All of the above exemplary POLYs, linkers, Y groups, and S groups are encompassed by the generalized structure for a thiol-selective polymer of the invention above. Preferably, X, a functional group resulting from the reaction of the electrophile of the polymer reagent and the nucleophile on the molecular reactant, is either an amide (—C(O)—NH—, or a urethane, —O—C(O)—NH—. In some instances, the functional group X is designated herein as "-$G_1$-C(O)-$G_2$-", where $G_1$ and $G_2$ are each independently a heteroatom such as O, NH, or S. In one embodiment, $G_1$ is absent, and Y corresponds to C(O)-G. Preferably, $G_2$ is —NH. Symmetrical polymer disulfides of the invention possess the generalized structure: (POLY-$L_{0,1}$-X—Y—S—)$_2$, II, which encompasses all of the herein described POLYs, linkers, and Y groups.

Storage of Polymer Reagents

Preferably, the thiol-selective polymers of the invention are stored under an inert atmosphere, such as under argon or under nitrogen. It is also preferable to minimize exposure of the polymers of the invention to moisture. Thus, preferred storage conditions are under dry argon or another dry inert gas at temperatures below about −15° C. Storage under low temperature conditions is preferred, since rates of undesirable side reactions are slowed at lower temperatures. In instances where the polymer segment of the polymer product is PEG, the PEG portion can react slowly with oxygen to form peroxides along the PEG portion of the molecule. Formation of peroxides can ultimately lead to chain cleavage, thus increasing the polydispersity of the PEG reagents provided herein. In view of the above, it is additionally preferred to store the polymers of the invention in the dark.

Thiol-activated Polymer Conjugates

The present invention also encompasses conjugates formed by reaction of any of the herein described thiol-selective polymers. In particular, the thiol-selective polymers of the invention are useful for conjugation to active agents or surfaces bearing at least one thiol or amino group available for reaction. Conjugates will possess the structure corresponding to functional groups formed by reacting any of the herein described thiol-selective groups, e.g., thiol, maleimide, vinylsulfone, orthopyridyldisulfide, with an accessible thiol contained in an active agent.

For instance, a conjugate of the invention may possess the following structure: POLY-$L_{0,1}$-X—Y—S—S-active agent, IV, where S—S— is a disulfide bond.

Alternatively, a conjugate of the invention may possess the following structure:

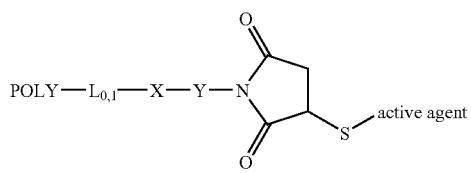

where "—S-active agent" represents an active agent, preferably a biologically active agent, comprising a thiol (—SH) group, and the other variables are as described previously. In instances where the active agent is a biologically active agent or small molecule containing only one reactive thiol group, the resulting composition may advantageously contain only a single polymer conjugate species, due to the relatively low number of sulfhydryl groups typically contained within a protein and accessible for conjugation. In some instances, a protein or small molecule or other active agent is engineered to possess a thiol group in a known position, and will similarly result in a composition comprising only a single polymer conjugate species. This approach is generally referred to as site-specific modification.

Alternatively, a conjugate of the invention may possess the following structure:

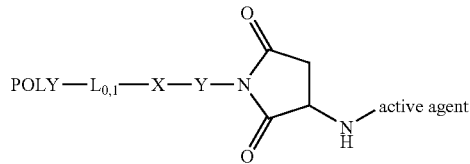

In the above structure, "—NH-active agent" represents an active agent or surface comprising an amino group, preferably a biologically active agent, and the other variables are as previously described. Under certain reaction conditions, maleimide groups can react with amino groups, such as those present in an active agent such as a protein.

A cysteine residue for coupling to an activated polymer of the invention may be naturally occurring (i.e., occurs in the protein in its native form) or may be inserted into the native sequence in place of a naturally-occurring amino acid using standard genetic engineering techniques. Since thiol groups are less numerous in proteins than are other typical polymer attachment sites such as amino groups, covalent attachment of a polymer derivative can result in more selective pegylation of the target protein. That is to say, the polymer derivatives of the invention can allow greater control over the resulting polymer conjugate—both in the number of polymer derivatives attached to the parent protein (mono versus di- versus tri-substituted conjugates, etc.) and the position of polymer attachment.

The generalized features of the conjugates of the invention have been described in detailed fashion above. Active agents that are covalently attached to a thiol-selective polymer encompass any of a number of types of molecules, entities, surfaces, and the like, as will become apparent from the following.

Target Molecules and Surfaces

The thiol-selective polymers of the invention may be attached, either covalently or non-covalently, to a number of entities including films, chemical separation and purification surfaces, solid supports, metal/metal oxide surfaces such as gold, titanium, tantalum, niobium, aluminum, steel, and their oxides, silicon oxide, macromolecules, and small molecules. Additionally, the polymers and methods of the invention may also be used in biochemical sensors, bioelectronic switches, and gates. The polymers and methods of the invention may also be employed in preparing carriers for peptide synthesis, for the preparation of polymer-coated surfaces and polymer grafts, to prepare polymer-ligand conjugates for affinity partitioning, to prepare cross-linked or non-cross-linked hydrogels, and to prepare polymer-cofactor adducts for bioreactors.

A biologically active agent for use in providing a conjugate of the invention may be any one or more of the following. Suitable agents may be selected from, for example, hypnotics and sedatives, psychic energizers, tranquilizers, respiratory drugs, anticonvulsants, muscle relaxants, antiparkinson agents (dopamine antagnonists), analgesics, anti-inflammatories, antianxiety drugs (anxiolytics), appetite suppressants, antimigraine agents, muscle contractants, anti-infectives (antibiotics, antivirals, antifungals, vaccines) antiarthritics, antimalarials, antiemetics, anepileptics, bronchodilators, cytokines, growth factors, anti-cancer agents, antithrombotic agents, antihypertensives, cardiovascular drugs, antiarrhythmics, antioxicants, anti-asthma agents, hormonal agents including contraceptives, sympathomimetics, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents.

More particularly, the active agent may fall into one of a number of structural classes, including but not limited to small molecules (preferably insoluble small molecules), peptides, polypeptides, proteins, antibodies, polysaccharides, steroids, nucleotides, oligonucleotides, polynucleotides, fats, electrolytes, and the like. Preferably, an active agent for coupling to a polymer of the invention possesses a native sulfydryl group or less preferably a native amino group, or alternatively, is modified to contain at least one reactive sulfhydryl group or amino group suitable for coupling.

Specific examples of active agents include but are not limited to aspariginase, amdoxovir (DAPD), antide, becaplermin, calcitonins, cyanovirin, denileukin diftitox, erythropoietin (EPO), EPO agonists (e.g., peptides from about 10-40 amino acids in length and comprising a particular core sequence as described in WO 96/40749), dornase alpha, erythropoiesis stimulating protein (NESP), coagulation factors such as Factor V, Factor VII, Factor VIIa, Factor VIII, Factor IX, Factor X, Factor XII, Factor XIII, von Willebrand factor; ceredase, cerezyme, alpha-glucosidase, collagen, cyclosporin, alpha defensins, beta defensins, exedin-4, granulocyte colony stimulating factor (GCSF), thrombopoietin (TPO), alpha-1 proteinase inhibitor, elcatonin, granulocyte macrophage colony stimulating factor (GMCSF), fibrinogen, filgrastim, growth hormones human growth hormone (hGH), growth hormone releasing hormone (GHRH), GRO-beta, GRO-beta antibody, bone morphogenic proteins such as bone morphogenic protein-2, bone morphogenic protein-6, OP-1; acidic fibroblast growth factor, basic fibroblast growth factor, CD-40 ligand, heparin, human serum albumin, low molecular weight heparin (LMWH), interferons such as interferon alpha, interferon beta, interferon gamma, interferon omega, interferon tau, consensus interferon; interleukins and interleukin receptors such as interleukin-1 receptor, interleukin-2, interluekin-2 fusion proteins, interleukin-2 receptor antagonist, interleukin-3, interleukin-4, interleukin-4 receptor, interleukin-6, interleukin-8, interleukin-12, interleukin-13 receptor, interleukin-17 receptor; lactoferrin and lactoferrin fragments, luteinizing hormone releasing hormone (LHRH), insulin, pro-insulin, insulin analogues (e.g., mono-acylated insulin as described in U.S. Pat. No. 5,922, 675), amylin, C-peptide, somatostatin, somatostatin analogs including octreotide, vasopressin, follicle stimulating hormone (FSH), influenza vaccine, insulin-like growth factor (IGF), insulintropin, macrophage colony stimulating factor (M-CSF), plasminogen activators such as alteplase, urokinase, reteplase, streptokinase, pamiteplase, lanoteplase, and teneteplase; nerve growth factor (NGF), osteoprotegerin, platelet-derived growth factor, tissue growth factors, transforming growth factor-1, vascular endothelial growth factor, leukemia inhibiting factor, keratinocyte growth factor (KGF), glial growth factor (GGF), T Cell receptors, CD molecules/antigens, tumor necrosis factor (TNF), monocyte chemoattractant protein-1, endothelial growth factors, parathyroid hormone (PTH), glucagon-like peptide, somatotropin, thymosin alpha 1, thymosin alpha 1 IIb/IIIa inhibitor, thymosin beta 10, thymosin beta 9, thymosin beta 4, alpha-1 antitrypsin, phosphodiesterase (PDE) compounds, VLA-4 (very late antigen-4), VLA-4 inhibitors, bisphosponates, respiratory syncytial virus antibody, cystic fibrosis transmembrane regulator (CFTR) gene, deoxyreibonuclease (Dnase), bactericidal/permeability increasing protein (BPI), and anti-CMV antibody. Exemplary monoclonal antibodies include etanercept (a dimeric fusion protein consisting of the extracellular ligand-binding portion of the human 75 kD TNF receptor linked to the Fc portion of IgG1), abciximab, afeliomomab, basiliximab, daclizumab, infliximab, ibritumomab tiuexetan, mitumomab, muromonab-CD3, iodine 131 tositumomab conjugate, olizumab, rituximab, and trastuzumab (herceptin).

Additional agents suitable for covalent attachment to a polymer include but are not limited to amifostine, amiodarone, aminocaproic acid, aminohippurate sodium, aminoglutethimide, aminolevulinic acid, aminosalicylic acid, amsacrine, anagrelide, anastrozole, asparaginase, anthracyclines, bexarotene, bicalutamide, bleomycin, buserelin, busulfan, cabergoline, capecitabine, carboplatin, carmustine, chlorambucin, cilastatin sodium, cisplatin, cladribine, clodronate, cyclophosphamide, cyproterone, cytarabine, camptothecins, 13-cis retinoic acid, all trans retinoic acid; dacarbazine, dactinomycin, daunorubicin, deferoxamine, dexamethasone, diclofenac, diethylstilbestrol, docetaxel, doxorubicin, epirubicin, estramustine, etoposide, exemestane, fexofenadine, fludarabine, fludrocortisone, fluorouracil, fluoxymesterone, flutamide, gemcitabine, epinephrine, L-Dopa, hydroxyurea, idarubicin, ifosfamide, imatinib, irinotecan, itraconazole, goserelin, letrozole, leucovorin, levamisole, lisinopril, lovothyroxine sodium, lomustine, mechlorethamine, medroxyprogesterone, megestrol, melphalan, mercaptopurine, metaraminol bitartrate, methotrexate, metoclopramide, mexiletine, mitomycin, mitotane, mitoxantrone, naloxone, nicotine, nilutamide, octreotide, oxaliplatin, pamidronate, pentostatin, pilcamycin, porfimer, prednisone, procarbazine, prochlorperazine, ondansetron, raltitrexed, sirolimus, streptozocin, tacrolimus, tamoxifen, temozolomide, teniposide, testosterone, tetrahydrocannabinol, thalidomide, thioguanine, thiotepa, topotecan, tretinoin, valrubicin, vinblastine, vincristine, vindesine, vinorelbine, dolasetron, granisetron; formoterol, fluticasone, leuprolide, midazolam, alprazolam, amphotericin B, podophylotoxins, nucleoside antivirals, aroyl hydrazones, sumatriptan; macrolides such as erythromycin, oleandomycin, troleandomycin, roxithromycin, clarithromycin, davercin, azithromycin, flurithromycin, dirithromycin, josamycin, spiromycin, midecamycin, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, grepafloxacin, gatifloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin; aminoglycosides such as gentamicin, netilmicin, paramecin, tobramycin, amikacin, kanamycin, neomycin, and streptomycin, vancomycin, teicoplanin, rampolanin, mideplanin, colistin, daptomycin, gramicidin, colistimethate; polymixins such as polymixin B, capreomycin, bacitracin, penems; penicillins including penicllinase-sensitive agents like penicillin G, penicillin V; penicllinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefoperazone, cefotetan, cefmetazole, ceftazidime, loracarbef, and moxalactam, monobactams like aztreonam; and carbapenems such as imipenem, meropenem, pentamidine isethiouate, albuterol sulfate, lidocaine, metaproterenol sulfate, beclomethasone diprepionate, triamcinolone acetamide, budesonide acetonide, fluticasone, ipratropium bromide, flunisolide, cromolyn sodium, and ergotamine tartrate; taxanes such as paclitaxel; SN-38, and tyrphostines.

Preferred peptides or proteins for coupling to a thiol-selective polymer of the invention include EPO, IFN-α, IFN-β, IFN-γ, consensus IFN, Factor VII, Factor VIII, Factor IX, EL-2, remicade (infliximab), Rituxan (rituximab), Enbrel (etanercept), Synagis (palivizumab), Reopro (abciximab), Herceptin (trastuzimab), tPA, Cerizyme (imiglucerase), Hepatitus-B vaccine, rDNAse, alpha-i proteinase inhibitor, GCSF, GMCSF, hGH, insulin, FSH, and PTH.

The above exemplary biologically active agents are meant to encompass, where applicable, analogues, agonists, antagonists, inhibitors, isomers, and pharmaceutically acceptable salt forms thereof. In reference to peptides and proteins, the invention is intended to encompass synthetic, recombinant, native, glycosylated, and non-glycosylated forms, as well as biologically active fragments thereof. The above biologically active proteins are additionally meant to encompass variants having one or more amino acids substituted (e.g., cysteine), deleted, or the like, as long as the resulting variant protein possesses at least a certain degree of activity of the parent (native) protein.

The conjugates or methods described herein can also be extended to hydrogel formulations.

Methods of Conjugation

Suitable conjugation conditions are those conditions of time, temperature, pH, reagent concentration, solvent, and the like sufficient to effect conjugation between a polymeric reagent and an active agent. As is known in the art, the specific conditions depend upon, among other things, the active agent, the type of conjugation desired, the presence of other materials in the reaction mixture and so forth. Sufficient conditions for effecting conjugation in any particular case can be determined by one of ordinary skill in the art upon a reading of the disclosure herein, reference to the relevant literature, and/or through routine experimentation.

Exemplary conjugation conditions include carrying out the conjugation reaction at a pH of from about 6 to about 10, and at, for example, a pH of about 6.0, 6.5, 7.0, 7.5, 8.0, 8.5, 9.0, 9.5, or 10. The reaction is allowed to proceed from about 5 minutes to about 72 hours, preferably from about 30 minutes to about 48 hours, and more preferably from about 4 hours to about 24 hours or less. Temperatures for conjugation reactions are typically, although not necessarily, in the range of from about 0° C. to about 40° C.; conjugation is often carried out at room temperature or less. Conjugation reactions are often carried out in a buffer such as a phosphate or acetate buffer or similar system.

With respect to reagent concentration, an excess of the polymeric reagent is typically combined with the active agent. In some cases, however, it is preferred to have stoichiometic amounts of the number of reactive groups on the polymeric reagent to the amount of active agent. Exemplary ratios of polymeric reagent to active agent include molar ratios of about 1:1 (polymeric reagent:active agent), 1.5:1, 2:1, 3:1, 4:1, 5:1, 6:1, 8:1, or 10:1. The conjugation reaction is allowed to proceed until substantially no further conjugation occurs, which can generally be determined by monitoring the progress of the reaction over time.

Progress of the reaction can be monitored by withdrawing aliquots from the reaction mixture at various time points and analyzing the reaction mixture by SDS-PAGE or MALDI-TOF mass spectrometry or any other suitable analytical method. Once a plateau is reached with respect to the amount of conjugate formed or the amount of unconjugated polymer remaining, the reaction is assumed to be complete. Typically, the conjugation reaction takes anywhere from minutes to several hours (e.g., from 5 minutes to 24 hours or more). The resulting product mixture is preferably, but not necessarily purified, to separate out excess reagents, unconjugated reactants (e.g., active agent) undesired multi-conjugated species, and free or unreacted polymer. The resulting conjugates can then be further characterized using analytical methods such as MALDI, capillary electrophoresis, gel electrophoresis, and/or chromatography.

More preferably, a thiol-selective polymer of the invention is typically conjugated to a sulfhydryl-containing active agent at pHs ranging from about 6-9 (e.g., at 6, 6.5, 7, 7.5, 8, 8.5, or 9), more preferably at pHs from about 7-9, and even more preferably at pHs from about 7 to 8. Generally, a slight molar excess of polymer reagent is employed, for example, a 1.5 to 15-fold molar excess, preferably a 2-fold to 10 fold molar excess. Reaction times generally range from about 15 minutes to several hours, e.g., 8 or more hours, at room temperature. For sterically hindered sulfhydryl groups, required reaction times may be significantly longer. Since the polymers of the invention are thiol-selective, thiol-selective conjugation is preferably conducted at pHs around 7.

Separation

Optionally, conjugates produced by reacting a thiol-selective polymer of the invention with a biologically active agent are purified to obtain/isolate different species, e.g., PEG-species, or to remove undesirable reaction side-products.

If desired, PEG conjugates having different molecular weights can be isolated using gel filtration chromatography. While this approach can be used to separate PEG conjugates having different molecular weights, this approach is generally ineffective for separating positional isomers having different pegylation sites within a protein. For example, gel filtration chromatography can be used to separate from each other mixtures of PEG 1-mers, 2-mers, 3-mers, etc., although each of the recovered PEG-mer compositions may contain PEGs attached to different reactive groups within the protein.

Gel filtration columns suitable for carrying out this type of separation include Superdex™ and Sephadex™ columns available from Amersham Biosciences. Selection of a particular column will depend upon the desired fractionation range desired. Elution is generally carried out using a non-amine based buffer, such as phosphate, acetate, or the like. The collected fractions may be analysed by a number of different methods, for example, (i) OD at 280 nm for protein content, (ii) BSA protein analysis, (iii) iodine testing for PEG content (Sims G. E. C., et al., *Anal. Biochem*, 107, 60-63, 1980), or alternatively, (iv) by running an SDS PAGE gel, followed by staining with barium iodide.

Separation of positional isomers can be carried out by reverse phase chromatography using, for example, an RP-HPLC C18 column (Amersham Biosciences or Vydac) or by ion exchange chromatography using an ion exchange column, e.g., a Sepharose™ ion exchange column available from Amersham Biosciences. Either approach can be used to separate PEG-biomolecule isomers having the same molecular weight (positional isomers).

Depending upon the intended use for the resulting PEG-conjugates, following conjugation, and optionally additional separation steps, the conjugate mixture may be concentrated, sterile filtered, and stored at low temperatures from about −20° C. to about −80° C. Alternatively, the conjugate may be lyophilized, either with or without residual buffer and stored as a lyophilized powder. In some instances, it is preferable to exchange a buffer used for conjugation, such as sodium acetate, for a volatile buffer such as ammonium carbonate or ammonium acetate, that can be readily removed during lyophilization, so that the lyophilized protein conjugate powder formulation is absent residual buffer. Alternatively, a buffer exchange step may be used using a formulation buffer, so that the lyophilized conjugate is in a form suitable for reconstitution into a formulation buffer and ultimately for administration to a mammal.

Pharmaceutical Compositions

The present invention also includes pharmaceutical preparations comprising a conjugate as provided herein in combination with a pharmaceutical excipient. Generally, the conjugate itself will be in a solid form (e.g., a precipitate) or in solution, which can be combined with a suitable pharmaceutical excipient that can be in either solid or liquid form.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The preparation may also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the preparation as well. Antioxidants are used to prevent oxidation, thereby preventing the deterioration of the conjugate or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant may be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; and chelating agents, such as EDTA, zinc and other such suitable cations.

Acids or bases may be present as an excipient in the preparation. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The pharmaceutical preparations encompass all types of formulations and in particular those that are suited for injection, e.g., powders that can be reconstituted as well as suspensions and solutions. The amount of the conjugate (i.e., the conjugate formed between the active agent and the polymer described herein) in the composition will vary depending on a number of factors, but will optimally be a therapeutically effective dose when the composition is stored in a unit dose container (e.g., a vial). In addition, the pharmaceutical preparation can be housed in a syringe. A therapeutically effective dose can be determined experimentally by repeated administration of increasing amounts of the conjugate in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient will be present in the composition in an amount of about 1% to about 99% by weight, preferably from about 5%-98% by weight, more preferably from about 15-95% by weight of the excipient, with concentrations less than 30% by weight most preferred.

These foregoing pharmaceutical excipients along with other excipients are described in "Remington: The Science & Practice of Pharmacy", $19^{th}$ ed., Williams & Williams, (1995), the "Physician's Desk Reference", $52^{nd}$ ed., Medical Economics, Montvale, N.J. (1998), and Kibbe, A. H., Handbook of Pharmaceutical Excipients, $3^{rd}$ Edition, American Pharmaceutical Association, Washington, D.C., 2000.

The pharmaceutical preparations of the present invention are typically, although not necessarily, administered via injection and are therefore generally liquid solutions or suspensions immediately prior to administration. The pharmaceutical preparation can also take other forms such as syrups, creams, ointments, tablets, powders, and the like. Other modes of administration are also included, such as pulmonary, rectal, transdermal, transmucosal, oral, intrathecal, subcutaneous, intra-arterial, and so forth.

As previously described, the conjugates can be administered injected parenterally by intravenous injection, or less preferably by intramuscular or by subcutaneous injection. Suitable formulation types for parenteral administration include ready-for-injection solutions, dry powders for combination with a solvent prior to use, suspensions ready for injection, dry insoluble compositions for combination with a vehicle prior to use, and emulsions and liquid concentrates for dilution prior to administration, among others.

Methods of Administering

The invention also provides a method for administering a conjugate as provided herein to a patient suffering from a condition that is responsive to treatment with conjugate. The method comprises administering, generally via injection, a therapeutically effective amount of the conjugate (preferably provided as part of a pharmaceutical preparation). The method of administering may be used to treat any condition that can be remedied or prevented by administration of the particular conjugate. Those of ordinary skill in the art appreciate which conditions a specific conjugate can effectively treat. The actual dose to be administered will vary depend upon the age, weight, and general condition of the subject as well as the severity of the condition being treated, the judgment of the health care professional, and conjugate being administered. Therapeutically effective amounts are known to those skilled in the art and/or are described in the pertinent reference texts and literature. Generally, a therapeutically effective amount will range from about 0.001 mg to 100 mg, preferably in doses from 0.01 mg/day to 75 mg/day, and more preferably in doses from 0.10 mg/day to 50 mg/day.

The unit dosage of any given conjugate (again, preferably provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Once the clinical endpoint has been achieved, dosing of the composition is halted.

One advantage of administering the conjugates of the present invention is that individual water-soluble polymer portions can be cleaved off. Such a result is advantageous when clearance from the body is potentially a problem because of the polymer size. Optimally, cleavage of each water-soluble polymer portion is facilitated through the use of physiologically cleavable and/or enzymatically degradable linkages such as urethane, amide, carbonate or ester-containing linkages. In this way, clearance of the conjugate (via cleavage of individual water-soluble polymer portions) can be modulated by selecting the polymer molecular size and the type functional group that would provide the desired clearance properties. One of ordinary skill in the art can determine the proper molecular size of the polymer as well as the cleavable functional group. For example, one of ordinary skill in the art, using routine experimentation, can determine a proper molecular size and cleavable functional group by first preparing a variety of polymer derivatives with different polymer weights and cleavable functional groups, and then obtaining the clearance profile (e.g., through periodic blood or urine sampling) by administering the polymer derivative to a patient and taking periodic blood and/or urine sampling. Once a series of clearance profiles have been obtained for each tested conjugate, a suitable conjugate can be identified.

All articles, books, patents, patent publications and other publications referenced herein are incorporated by reference in their entireties.

The following examples illustrate, but in no way are intended to limit the scope of the present invention.

EXAMPLES

Materials and Methods $^1$H NMR data was obtained using a 400 MHz spectrometer manufactured by Bruker.

PEG reagents referred to in the appended examples are available from Nektar Therapeutics, Huntsville, Ala.

1. Preparation of mPEG-5K Propionic Acid, N-hydroxysuccinimide (NHS) Ester.

The PEG reagent, mPEG-5K propionic acid, N-hydroxysuccinimide (NHS) ester, was synthesized as follows.

A. M-PEG(5,000)-Nitrile (1)

M-PEG-OH (methoxy-PEG, MW=5,000 daltons, 50 g, containing 4 wt % of higher molecular weight PEG-diol, as determined by Gel Permeation Chromatography(GPC), was dissolved in distilled water (50.0 ml) to which was added potassium hydroxide (1.0 g). The solution was cooled to 0-5° C. in an ice bath. Acrylonitrile (6.8 g) was added slowly, and the solution was stirred for 2.5 hours at 0-5° C. The pH of the solution was adjusted to 7 by addition of sodium dihydrogen phosphate. The product was extracted three times with dichloromethane (250, 100 and 50 ml). The combined organic layers were dried over magnesium sulfate, filtered, concentrated and the product was precipitated by addition to ethyl ether at 0-5° C. The precipitate was removed by filtration and dried under vacuum.

Yield 47.0 g. NMR (d6-DMSO): 2.74 ppm (t, 2H, —CH$_2$—CN); 3.21 ppm, (s, 3H, —OCH$_3$), 3.51 ppm (s, PEG backbone).

B. M-PEG(5,000)-Amide (2)

A mixture of M-PEG(5,000)-nitrile, (1), (47.0 g) and concentrated hydrochloric acid (235 g) was stirred at room temperature for 48 hours. The solution was diluted with two liters of water and extracted with dichloromethane (300, 200, and 100 ml). The combined organic extracts were washed twice with water, dried over sodium sulfate, filtered, and concentrated to dryness by rotary evaporation.

Yield 43.0 g. NMR (d$_6$-DMSO): 2.26 ppm (t, 2H, —CH$_2$—CONH$_2$); 2.43 ppm (t, 2H, —CH$_2$—COOH); 3.21 ppm (s, 3H, —OCH$_3$), 3.51 ppm (s, PEG backbone).

C. M-PEG(5,000)-Propionic Acid, (Alpha-methoxy, Omega-propionic Acid of PEG) (3)

M-PEG(5,000)-amide (2) (32.0 g) was dissolved in 2300 ml of distilled water to which was added 200 g of potassium hydroxide, and the solution was stirred for 22 hours at room temperature. Sodium chloride (300 g) was added, and the solution was extracted three times each with with 300 ml dichloromethane. The combined organic extracts were washed with 5% oxalic acid, water (twice), and dried over sodium sulfate. The solution was concentrated and the product precipitated by addition to ethyl ether. The product M-PEG(5,000)-propionic acid (3) was collected by filtration and dried over vacuum.

Yield 28.0 g. NMR (d$_6$-DMSO): 2.43 ppm (t, 2H, —CH$_2$—COOH); 3.21 ppm (s, 3H, —OCH$_3$), 3.51 ppm (s, PEG backbone).

Removal of Difunctional Impurities: M-PEG(5,000)-propionic acid (3) containing 4 wt % of PEG(10,000)-dipropionic acid (22 g) (derived from reaction of PEG diol impurity contained in the starting material) was dissolved in 2200 ml deionized water and the resulting solution was applied to a DEAE Sephadex A-25 chromatographic column in the tetraborate form. A stepwise ionic gradient of sodium chloride (from 2 to 14 mM at increments) was applied, and fraction collection (approx. 60 ml each) begun. Fractions 4-25 contained pure M-PEG(5,000)-propionic acid. The subsequent two fractions did not contain PEG, while fractions 28-36 contained the pure PEG(10,000)-dipropionic acid. The fractions containing pure M-PEG(5,000)-propionic acid were combined and concentrated (to approx. 100 ml). Sodium chloride (10 g) was added, the pH was adjusted to 3 and the product was extracted with dichloromethane. The organic layer was dried over MgSO$_4$, and the solvent was distilled off under reduced pressure to give 18.4 g of product.

HPLC analysis showed that the product was 100 % pure M-PEG(5,000)-propionic acid (absent any other impurities).

D. M-PEG(5,000)-Propionic Acid, NHS Ester, (Alpha-methoxy, Omega-propionic Acid Succinimidyl Ester of PEG ("methoxy-PEG-SPA")), (4)

M-PEG(5,000)-propionic acid (14.4 g), (3), was dissolved in dichloromethane (60 ml) to form a solution to which was added N-hydroxysuccinimide (0.36 g). The solution was cooled to 0° C., and a solution of dicyclohexylcarbodiimide (0.72 g) in 10 ml dichloromethane was added dropwise. The solution was stirred overnight at room temperature under an argon atmosphere. The reaction mixture was filtered, concentrated, and the product was precipitated by addition to ethyl ether.

Yield of final product (4): 14.0 g. NMR (d$_6$-DMSO): 2.81 ppm (s, 4H, NHS); 2.92 ppm (t, 2H, —CH$_2$—COO—); 3.21 ppm, (s, 3H, —OCH$_3$), 3.51 ppm (s, PEG backbone).

2. Preparation of mPEG-20K Butanoic Acid, N-hydroxysuccinimide (NHS) Ester.

The PEG reagent, mPEG-20K butanoic acid, N-hydroxysuccinimide (NHS) ester, was synthesized as follows.

A. M-PEG(20K)-Methanesulfonate (5)

M-PEG-OH (MW=20,000 daltons, 60 g, containing 6 wt % of higher molecular weight PEG-diol (determined by Gel Permeation Chromatography(GPC))) was dissolved in 300 ml of toluene and azeotropically distilled for 1 hour under argon atmosphere. Next the solution was cooled to room temperature. To the solution was added 24 ml of anhydrous dichloromethane and 0.62 ml of triethylamine (0.0044 moles). 0.28 ml of methanesulfonyl chloride (0.0036 moles) was added dropwise. The solution was stirred at room temperature under nitrogen atmosphere overnight. Sodium carbonate (30 g) was then added, and the mixture was stirred for 1 h. The solution was filtered and solvents were distilled off under reduced pressure. Yield 27.5 g $^1$H NNR (d$_6$-DMSO): 3.17 ppm (s, 3H, CH$_3$-methanesulfonate), 3.24 ppm (s, 3H, —CH$_3$), 3.51 ppm (s, PEG backbone), 4.30 ppm (m, —CH$_2$-methanesulfonate).

B. M-PEG(20,000)-Butanoic Acid (8)

Ethyl malonate (3.4 ml, 0.022 equivalents) dissolved in 200 ml of dioxane was added drop by drop to sodium hydride (0.536 g, 0.022 equivalents) and toluene (100 ml) in a round bottomed flask under nitrogen. M-PEG(20K)-methanesulfonate (5) (40 g, 0.0020 moles) dissolved in 100 ml of toluene was added to the above mixture. The resulting mixture was refluxed overnight. The reaction mixture was then concentrated to half its original volume, extracted with 50 ml of 10% aqueous NaCl solution, extracted with 50 ml of 1% aqueous hydrochloric acid, and the aqueous extracts combined. The collected aqueous layers were extracted with dichloromethane (150 ml×3), and the organic layer was dried over magnesium sulfate for 3 hours, filtered, and evaporated to dryness.

Yield: 36 g of M-PEG malonic acid diethyl ester (6). NMR (d$_6$-DMSO): 1.17 ppm (t, 6H, —CH$_3$); 1.99 ppm (quartet, 2H, —CH$_2$—CH); 3.21 ppm, (s, 3H, —OCH$_3$); 3.51 ppm (s, PEG backbone); 4.10 ppm (quintet, 4H, —OCH$_2$—CH$_3$).

M-PEG malonic acid diethyl ester (6) (36 g) was dissolved in 480 ml of 1N sodium hydroxide containing 24 g of sodium chloride, and the mixture was stirred for one hour. The pH of the mixture was adjusted to 3.0 by addition of 6N hydrochloric acid, and the mixture was extracted with dichloromethane (300 ml and 200 ml). The organic layer was dried over magnesium sulfate, filtered, concentrated, and poured into cold ethyl ether. The product M-PEG(20,000)-malonic acid (7) was removed by filtration and dried under vacuum.

Yield: 32 g. NMR (d$_6$-DMSO); 1.0 ppm (q, 2H, —CH$_2$CH$_2$CH—); 2.90 ppm (t, 2H, —CH$_2$CH—); 3.21 ppm (s, 3H, —OCH$_3$); 3.51 ppm (s, PEG backbone); 12.1 ppm (s, 2H, —COOH).

M-PEG malonic acid (7) (30 g) was dissolved in 240 ml of dioxane and refluxed for 8 hours, then concentrated to dryness. The residue was dissolved in 200 ml water, extracted with dichloromethane (140 ml and 100 ml), dried over magnesium sulfate, and the solution concentrated by rotary evaporation. The residue was precipitated by addition to cold ethyl ether.

Yield: 22 g of M-PEG(20,000)-butanoic acid (8). $^1$H NMR (d$_6$-DMSO): 1.72 ppm (quintet, 2H, —CH$_2$CH$_2$—COOH); 2.40 ppm (t, 4H, —CH$_2$CH$_2$—COOH); 3.21 ppm (s, 3H, —OCH$_3$); 3.51 ppm (s, PEG backbone). HPLC analysis showed that the product contained 94 wt % of M-PEG(20,000)-butanoic acid and 6 wt % of PEG-dibutanoic acid derived from higher molecular weight PEG-diol contained in the starting material To remove higher molecular weight reactive PEG species, M-PEG(20K)-butanoic acid containing 6 wt % of PEG-dibutanoic acid (22 g) was dissolved in 2200 ml deionized water and applied to a DEAE Sephadex A-50 column in the tetraborate form. A stepwise ionic gradient of sodium chloride (from 1 to 4 mM at increments) was applied, and fractions were collected. Fractions, containing pure M-PEG(20,000)-butanoic acid, were combined and collected. Later eluting fractions containing pure PEG-dibutanoic acid were set aside. The combined fractions containing pure M-PEG(20,000)-butanoic acid were concentrated (to approx. 200 ml). Sodium chloride (20 g) was added, the pH was adjusted to 3 and the product was extracted with dichloromethane. The extract was dried (MgSO$_4$), and the solvent was distilled off under reduced pressure to give 13.6 g of product.

HPLC analysis showed that the product is 100% pure M-PEG(20,000)-butanoic acid (8) absent higher molecular weight PEG species.

C. M-PEG(20,000)-Butanoic Acid, NHS Ester (9)

M-PEG(20,000)-butanoic acid (8) (13.6 g.) was dissolved in dichloromethane (40 ml) and N-hydroxysuccinimide (0.094 g) added to the solution. The solution was cooled at 0° C., and a solution of dicyclohexylcarbodiimide, DCC, (0.196 g) in 10 ml dichloromethane was added dropwise. The solution was stirred at room temperature overnight. The reaction mixture was filtered, concentrated, and precipitated by addition to ethyl ether.

Yield of final product: 13.1 g. NMR (d$_6$-DMSO): 1.83 ppm (quintet, 2H, —CH$_2$CH$_2$CH$_2$—COO—); 2.70 ppm (t, 2H, —CH$_2$—COO—); 2.81 ppm (4H, NHS); 3.21 ppm (s, 3H, —OCH$_3$); 3.51 ppm (s, PEG backbone).

Example 1

Preparation of mPEG (5K)-Thiol, MPEG(5K)-CH$_2$CH$_2$CONHCH$_2$CH$_2$SH (11)

Methoxy-PEG-5K-thiol was prepared in high purity and in high yield from an exemplary electrophilically activated PEG, mPEG-5K propionic acid, N-hydroxysuccinimide (NHS) ester (also referred to as mPEG-5K succinimidyl propionate), commercially available from Shearwater Corporation, now Nektar Therapeutics, (Shearwater Catalog 2001, Polyethylene Glycol and Derivatives for Biomedical Applications), Huntsville, Ala.

The preparation of mPEG-5K succinimidyl propionate is described generally in U.S. Pat. No. 5,672,662 (Shearwater Polymers), and in the "Materials and Methods" sections above.

Synthesis of M-PEG(5,000)-Thiol (11)

Reaction Scheme:

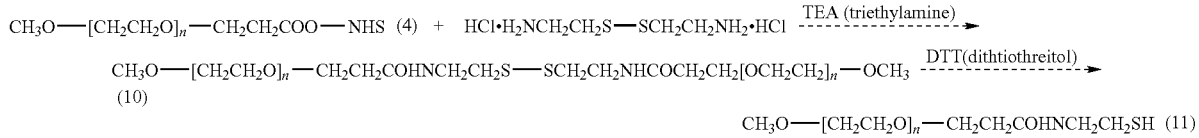

M-PEG propionic acid, NHS ester, (4), (MW=5,268, 10.0 g, 1.898 mmol) was dissolved in dichloromethane (100 ml) to which were added cystamine dihydrochloride (0.2278 g, 1.012 mmol) and triethylamine (0.66 ml). The solution was stirred overnight at room temperature under an atmosphere of argon. The Gel Permeation Chromatography (GPC) analysis showed the reaction mixture contained the desired product (10) (symmetrical disulfide having a molecular weight of about 10,000) in 97.53% yield and M-PEG(5,000)-Propionic Acid in 2.14% yield.

Dithiothreitol (DTT) (0.88 g, 0.005705 moles) and triethylamine (0.5 ml) were then added and the reaction mixture was stirred for 3 h at room temperature under argon. Next 2,6-di-tert-butyl-4-methylphenol (BHT) (0.05 g) was added and the solvent was distilled off under reduced pressure. The crude thiol product (11) was dissolved in dichloromethane (20 ml) and precipitated with isopropyl alcohol at 0-5° C. Yield after drying was 8.80 g.

GPC analysis: Desired product: M-PEG(5,000)-thiol, (11), 96.05% yield; M-PEG(5,000)-propionic acid, 0.57% yield; non-reduced dimer, (10), 3.07%. NMR ($d_6$-DMSO): 1.52 ppm (t, 1H, —SH); 2.31 ppm (t, 2H, —$CH_2$—CO—); 2.66 ppm (dt, 2H, —$CH_2$—S—); 3.21 ppm, (s, 3H, —$OCH_3$), 3.51 ppm (s, PEG backbone); 8.05 ppm (t, 1H, —NH—).

Both the exemplary disulfide intermediate, (10), and the reduced PEG-thiol product, (11), were prepared in high yield and in high purity using a simple reaction scheme requiring only two steps. The exemplary reagent, cystamine, is commercially available, and the amino group therein is readily substituted for the succinimidyl group on the carbonyl product. The exemplary use of a stoichiometric amount of symmetrical reagent having two terminal reactive amino groups makes the reaction "cleaner" due to the formation of only one substitution product not contaminated by excess of reagent. The resulting PEG-thiol product is suitable for coupling to a reactive thiol group, e.g., contained in a drug or in a cysteine residue of a protein, to form a corresponding PEG conjugate. The PEG linkages (i.e., the linker portion of the molecule connecting the PEG chain or backbone to a reactive thiol group on a drug or other species) described herein are stable and provide a new class of water-soluble, non-naturally occurring polymers suitable that can be readily synthesized, and that can be used to selectively modify or pegylate proteins or other reactive molecules without the need for multiple synthetic steps, protection-deprotection steps, and multiple purifications.

Example 2

Preparation of mPEG (20K)-Thiol, $CH_3O$ $(CH_2CH_2O)_n(20K)$-$CH_2CH_2CH_2CONHCH_2CH_2SH$ (13)

Methoxy-PEG-20K-thiol was prepared in high purity and in high yield from another exemplary electrophilically activated PEG, mPEG-20K butanoic acid, N-hydroxysuccinimide (NHS) ester (also referred to as mPEG-20K succinimidyl butanoate), commercially available from Shearwater Corporation, now Nektar Therapeutics (Shearwater Catalog 2001, Polyethylene Glycol and Derivatives for Biomedical Applications), Huntsville, Ala.

The preparation of mPEG-5K succinimidyl butanoate is described generally in U.S. Pat. No. 5,672,662 (Shearwater Polymers), and in the "Materials and Methods" sections above.

Synthesis of m-PEG(20,000)-Thiol (13)

Reaction Sheme

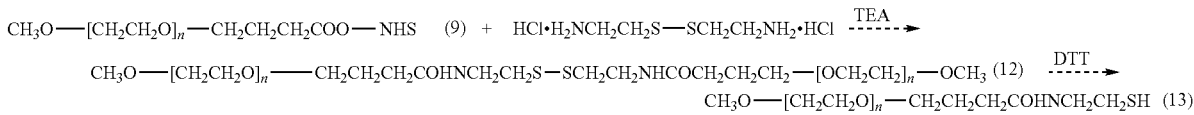

M-PEG(20K)-butanoic acid, NHS ester (9) (MW=20,000 daltons, 10.0 g, 0.500 mmol) was dissolved in dichloromethane (100 ml) and cystamine dihydrochloride (0.0564 g, 0.251 mmoles) and triethylamine (0.167 ml) were added. The solution was stirred overnight at room temperature under an atmosphere of argon. The GPC analysis showed that the reaction mixture contained the desired product (dimer having molecular weight about 40,000, (12)) 98.5% pure and 1.5% M-PEG(20,000)-butanoic acid.

Dithiothreitol (DTT) (0.23 g, 1.500 mmoles) and triethylamine (0.5 ml) were added and the reaction mixture was stirred for 3 h at room temperature under an argon atmosphere. Next BHT (0.05 g) was added and the solvent was distilled under reduced pressure. The crude product was dissolved in dichloromethane (20 ml) and precipitated with isopropyl alcohol at 0-5° C.

Yield after drying 9.20 g. HPLC analysis: M-PEG(20K)-Thiol (13) 96.0%, M-PEG(20,000)-butanoic acid 1.5%, non-reduced dimer 2.5%.

Similar to Example 1 above, this example demonstrates the preparation of yet another representative PEG-thiol (as well as its corresponding disulfide precursor). The synthesis is straightforward, requiring only two reaction steps: substitution of the representative nucleophilic amino group on cystamine at the electrophilic carbonyl carbon on the illustrative PEG reagent, (9), followed by reduction of the disulfide to yield the corresponding PEG-thiol. The use of a symmetrical disulfide reagent simplifies the synthesis, making purification of the PEG-thiol product unnecessary. The PEG-thiol is formed in high yield (greater than 90%, in fact greater than 95%), and is suitable for coupling with reactive thiol groups e.g., contained in cysteine residues of therapeutic proteins, or introduced by chemical means into a protein or polypeptide, or present in small molecules or other active agents.

Example 3

Preparation of PEG(40K)-Di-Thiol, HSCH$_2$CH$_2$NH(O)CCH$_2$O-PEG-40K-CH$_2$C(O)HNCH$_2$CH$_2$SH (18)

PEG-40K-di-thiol (18) was prepared from a bifunctional PEG reagent, PEG-40K dicarboxylic acid, as set forth below.

reduced pressure. HPLC analysis: PEG (40,000)-Di-Carboxylic Acid 86.5%, PEG (40,000)-Mono-Carboxylic Acid 13.0%, HO-PEG(40,000)-OH 0.5%.

Yield 33.1 g. $^1$H NMR (d$_6$-DMSO): 3.51 ppm (s, PEG backbone); 4.02 ppm (4H, —OCH$_2$COO—)

The obtained product (30 g) was dissolved in 3000 ml deionized water and applied to a DEAE Sephadex A-50 chromatographic column in the tetraborate form. A stepwise ionic gradient of sodium chloride (from 2 to 10 mM at increments) was applied, and fractions were collected. Fractions positive to the PAA test, i.e., containing PEG (40,000)-di-carboxylic acid, were combined and concentrated (to approx. 300 ml). Sodium chloride (30 g) was added, the pH was adjusted to 3 and the product was extracted with dichloromethane. The extract was dried (MgSO$_4$), and the solvent was distilled off under reduced pressure to give 21.6 g of product, (15). The product (15) was shown to be pure di-acid, i.e., 100% PEG (40,000)-di-carboxylic acid, by HPLC.

C. PEG(40,000)-Di-Carboxylic Acid, NHS ester, (16)

PEG (40,000)-di-carboxylic acid (15) (20 g) was dissolved in dichloromethane (200 ml) to which was added N-hydroxysuccinimide (0.138 g). The solution was cooled to 0° C., a solution of dicyclohexylcarbodiimide (0.290 g) in 5 ml dichloromethane was added dropwise, and the solution was stirred at room temperature overnight. The reaction mixture was filtered, concentrated, and precipitated by addition to ethyl ether. Yield of final product, (16): 18.3 g.

$^1$H NMR (d$_6$-DMSO): 2.83 ppm (8H, NHS); 3.51 ppm (s, PEG backbone); 4.61 ppm (4H, —OCH$_2$COO—).

D. PEG(40.000)-Di-Thiol (18)

Reaction Scheme

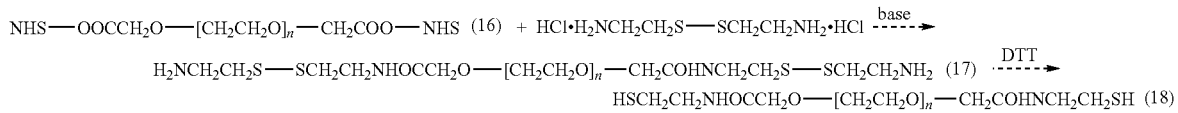

A. PEG (40.000)-Di-Carboxylic Acid, Ethyl Ester, (14)

HO-PEG-OH (MW=40,000 daltons, 50 g, 2.50 hydroxy mequiv.) was dissolved in 750 ml of toluene and azeotropically distilled for 1 hour under argon atmosphere. 150 ml toluene was distilled from the reaction mixture. Next the solution was cooled to 40° C. and 1.0 M solution of potassium tert-butoxide in tert-butanol (4.0 ml, 4 mmoles) was added, followed by addition of ethyl bromoacetate (1.4 g, 8.4 mmoles). The reaction mixture was stirred overnight at room temperature under a nitrogen atmosphere. The solvent was distilled off under reduced pressure, and the crude product dissolved in dichloromethane and added to ethyl ether. The precipitated product was isolated by filtration and dried under reduced pressure. Yield 42.3 g.

B. PEG (40,000)-Di-Carboxylic Acid (15)

A solution of 40.0 grams (1.0 mmoles) of PEG (40,000)-dicarboxylic acid ethyl ester (14) in 400 ml 1M NaOH was stirred at room temperature for 3 hours. Next the pH of the mixture was adjusted to 2 and the product was extracted with dichloromethane. The solvents were then distilled off under reduced pressure. The crude product was dissolved in dichloromethane (100 ml) and added to ethyl ether (900 ml). The precipitated product was isolated by filtration and dried under PEG(40,000)-di-carboxylic acid, NHS ester (16) (MW=40,000, 18.0 g, 0.900 mequiv.) was dissolved in dichloromethane (150 ml) and cystamine dihydrochloride (1.01 g, 4.5 mmoles) and triethylamine (1.70 ml) were added. The solution was stirred overnight at room temperature under argon atmosphere. The solution was concentrated and added to 900 ml of isopropyl alcohol at room temperature. The precipitated product was removed by filtration and dried under reduced pressure.

NMR analysis showed that all NHS ester was consumed and the desired disulfide product (17) was formed. The product was dissolved in dichloromethane (150 ml), dithiothreitol (DTT) (0.84 g, 5.446 mmoles) and triethylamine (2.0 ml) were added and the reaction mixture was stirred 3 h at room temperature under an argon atmosphere. Next BHT (0.09 g) was added and the solvent was distilled off under reduced pressure. The residue—a crude dithiol product (18) was dissolved in dichloromethane (40 ml) and precipitated with isopropyl alcohol at room temperature. Yield after drying 14.3 g.

$^1$H NMR (d$_6$-DMSO): 1.07 ppm (t, 2H, —SH); 2.66 ppm (dt, 4H, —CH$_2$—S—); 3.51 ppm (s, PEG backbone); 3.90 ppm (s, 4H, —OCH$_2$CO—, 8.05 ppm (t, 2H, —NH—).

It is claimed:

1. A method for preparing a thiol-selective derivative of a water-soluble polymer, said method comprising:

reacting a water-soluble polymer comprising a water-soluble polymer segment ("POLY") having one terminus activated with an electrophile ("—E") with a molecule of the structure "NU—Y—S, comprising a nucleophile ("—NU") and a thiol-selective moiety ("—S") selected from the group consisting of thiol, protected thiol, symmetrical disulfide, maleimide, and iodoacetamide, and a linear group ("—Y—") interposed between NU and S, under conditions effective to promote reaction between said electrophile and said nucleophile to form a polymer product comprising a thiol-selective terminus selected from the group consisting of thiol, protected thiol, disulfide, maleimide, and iodoacetamide ("POLY—S"), wherein the molecular mass of the water-soluble polymer segment is from 1,000 Daltons to 50,000 Daltons.

2. The method of claim 1, wherein said thiol-selective moiety is a disulfide, and said method further comprises the step of reducing the disulfide bond in said POLY-S to form a polymer having a terminal thiol (POLY-SH).

3. The method of claim 1, wherein said water-soluble polymer segment is selected from the group consisting of poly (alkylene oxide), poly(vinyl pyrrolidone), poly(vinyl alcohol), polyoxazoline, poly(acryloylmorpholine), and poly (oxyethylated polyol).

4. The method of claim 1, wherein the POLY-S product from step (ii) comprises greater than about 95% by weight mono-functionally substituted POLY-S.

5. The method of claim 1, wherein the POLY-S product from step (ii) comprises less than about 5% di-functionally-substituted POLY-S.

6. The method of claim 3, wherein the water-soluble polymer segment is a polyalkylene oxide.

7. The method of claim 6, wherein said-water soluble polymer segment is a polyethylene glycol (PEG).

8. The method of claim 7, wherein said polyethylene glycol is end-capped.

9. The method of claim 1, wherein said electrophile is a carboxylic acid or a carboxylic acid derivative.

10. The method of claim 1, wherein said electrophile is selected from the group consisting of carboxylic acid ester, carbonate ester, carbonic acid, acid halide, and anhydride.

11. The method of claim 1, further comprising the step of purifying said water-soluble polymer prior to said reacting.

12. The method of claim 9, further comprising the step of purifying said water-soluble polymer prior to said reacting.

13. The method of claim 11, wherein said purifying step comprises a chromatographic or a chemical separation.

14. The method of claim 12, wherein said purifying step comprises ion exchange chromatography.

15. The method of claim 6, wherein said water-soluble polymer contains less than about 5% polyalkylene oxide dial.

16. The method of claim 1, wherein said nucleophile is selected from the group consisting of primary amino, secondary amino, hydroxy, imino, thiol, and thioester.

17. The method of claim 16, wherein said nucleophile is primary or secondary amino.

18. The method of claim 7, wherein said polymer comprises an end-capping group selected from the group consisting of alkoxy, substituted alkoxy, alkenyloxy, substituted alkenyloxy, alkynyloxy, substituted alkynyloxy, aryloxy, and substituted aryloxy.

19. The method of claim 7, wherein said water-soluble polymer is an N-hydroxysuccinimidyl propionate or an N-hydroxysuccinimidyl butanoate of polyethylene glycol.

20. The method of claim 1, wherein said molecule is cystamine or cysteamine.

21. The method of claim 1, wherein said thiol selective moiety is thiol, and said method further comprises the step of reacting said POLY-S thiol with a thiol or protected thiol group of a protein to form a disulfide-linked polymer-protein conjugate ("POLY-S—S-protein").

22. The method of claim 2, further comprising the step of reacting said POLY-SH with a thiol or protected thiol group of a protein to form a disulfide-linked polymer-protein conjugate ("POLY-S—S-protein").

23. The method of claim 7, wherein said polyethylene glycol has a structure selected from the group consisting of linear, branched, forked, and multi-armed.

24. The method of claim 7, wherein said polyethylene glycol comprises a hydrolyzable linkage.

25. The method of claim 1, wherein said molecule is a symmetrical disulfide reagent comprising a nucleophile (-NU), and said reacting step results in formation of a symmetrical water-soluble polymer having a central disulfide bond.

26. A water-soluble polymer having a thiol-selective terminus (POLY-S) produced by a method comprising:

reacting a water-soluble polymer comprising a water-soluble polymer segment ("POLY") having one terminus activated with an electrophile ("-E") with a molecule of the structure "NU-Y—S, comprising a nucleophile ("-NU") and a thiol-selective moiety ("—S") selected from the group consisting of thiol, protected thiol, disulfide, maleimide, and iodoacetamide, and a linear group ("—Y—") interposed between NU and S, under conditions effective to promote reaction between said electrophile and said nucleophile to form a polymer product comprising a thiol-selective terminus selected from the group consisting of thiol, protected thiol, disulfide, maleimide, and iodoacetamide ("POLY-S"), wherein the molecular mass of the water-soluble polymer segment is from 1,000 Daltons to 50,000 Daltons.

27. An activated polymer comprising the structure:

POLY-L-C(O)G-Y—S—W, wherein POLY is a water-soluble polymer segment,

L is a linker,

G is a heteroatom selected from the group consisting of O, NH, and S,

Y is selected from the group consisting of $C_2$-$C_{10}$ alkylene, substituted alkylene, cycloalkylene, substituted cycloalkylene, aryl, and substituted aryl, S is a sulfur atom, and W is H or a protecting group, wherein the molecular mass of the water-soluble polymer segment is from 1,000 Daltons to 50,000 Daltons.

28. The activated polymer of claim 27, wherein POLY is a polyalkylene glycol.

29. The activated polymer of claim 27, wherein POLY is a polyethylene glycol, L is —$CH_2$—, G is N(H), and Y is —$(CH_2)_2$—.

30. The activated polymer of claim 27, wherein L is an aliphatic linker comprising from one to 10 carbon atoms.

31. The activated polymer of claim 27, wherein L is a linker selected from the group consisting of $(CH_2)_{2, 3, 4\ and\ 5}$.

32. The activated polymer of claim 28, wherein said polyethylene glycol has a structure selected from the group consisting of linear, branched, forked, and multi-armed.

33. The activated polymer of claim 28, comprising the structure:

W—S—Y-G-(O)C-L-POLY-L-C(O)G-Y—S—W.

34. An activated polymer comprising the structure:

POLY-L-C(O)G-Y-Q, wherein POLY is a water-soluble polymer segment,

L is a linker,

G is a heteroatom selected from the group consisting of O, NH, and S,

Y is selected from the group consisting of $C_2$-$C_{10}$ alkylene, substituted alkylene, cycloalkylene, substituted cycloalkylene, aryl, and substituted aryl, and Q is selected from the group consisting of thiol, protected thiol, maleimide, and iodoacetamide, wherein the molecular mass of the water-soluble polymer segment is from 1,000 Daltons to 50,000 Daltons.

35. A composition comprising the activated polymer of any one of claims 27 to 34.

36. The composition of claim 35, comprising greater than about 95% by weight monofunctional product.

37. A polymer-conjugate comprising the structure:

POLY-L-C(O)G-Y—S—S-Drug wherein POLY is a water-soluble polymer segment,

L is a linker,

G is a heteroatom selected from the group consisting of O, NH, and S, and

Y is selected from the group consisting of $C_2$-$C_{10}$ alkylene, substituted alkylene, cycloalkylene, substituted cycloalkylene, aryl, and substituted aryl, wherein the molecular mass of the water-soluble polymer segment is from 1,000 Daltons to 50,000 Daltons.

38. The polymer conjugate of claim 37, wherein said drug is selected from the group consisting of proteins, peptides, and small molecules.

39. A composition comprising the polymer conjugate of claim 37.

40. The composition of claim 39 further comprising a pharmaceutical excipient.

41. A method for delivering a drug to a subject in need thereof, said method comprising administering the polymer-conjugate of claim 37.

* * * * *

UNITED STATES PATENT AND TRADEMARK OFFICE
CERTIFICATE OF CORRECTION

| | | |
|---|---|---|
| PATENT NO. | : 7,910,661 B2 | Page 1 of 1 |
| APPLICATION NO. | : 10/753047 | |
| DATED | : March 22, 2011 | |
| INVENTOR(S) | : Kozlowski et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1406 days.

Signed and Sealed this
Sixteenth Day of August, 2011

David J. Kappos
*Director of the United States Patent and Trademark Office*